(12) United States Patent
Kitagawa et al.

(10) Patent No.: US 11,266,317 B2
(45) Date of Patent: Mar. 8, 2022

(54) BLOOD PRESSURE MEASUREMENT DEVICE

(71) Applicants: OMRON HEALTHCARE CO., LTD., Kyoto (JP); OMRON CORPORATION, Kyoto (JP)

(72) Inventors: Tsuyoshi Kitagawa, Kyoto (JP); Shingo Yamashita, Kyoto (JP); Toshihiko Ogura, Kyoto (JP); Masayuki Fukutsuka, Kyoto (JP); Daizo Oka, Kyoto (JP); Naomi Matsumura, Kyoto (JP); Kentaro Mori, Kyoto (JP); Hiroyuki Kinoshita, Kyoto (JP); Masayuki Wakamiya, Kyoto (JP)

(73) Assignees: OMRON HEALTHCARE Co., Ltd., Kyoto (JP); Omron Corporation, Kyoto (JP)

( * ) Notice: Subject to any disclaimer, the term of this patent is extended or adjusted under 35 U.S.C. 154(b) by 563 days.

(21) Appl. No.: 15/499,379

(22) Filed: Apr. 27, 2017

(65) Prior Publication Data

US 2017/0224227 A1    Aug. 10, 2017

Related U.S. Application Data

(63) Continuation of application No. PCT/JP2015/078538, filed on Oct. 7, 2015.

(30) Foreign Application Priority Data

Oct. 31, 2014  (JP) .............................. JP2014-223249

(51) Int. Cl.
*A61B 5/022* (2006.01)
*A61B 5/00* (2006.01)
(Continued)

(52) U.S. Cl.
CPC .......... *A61B 5/022* (2013.01); *A61B 5/02108* (2013.01); *A61B 5/6824* (2013.01);
(Continued)

(58) Field of Classification Search
CPC ....... A61B 5/02; A61B 5/021; A61B 5/02108; A61B 5/02116; A61B 5/02225; A61B 5/0225; A61B 5/022; A61B 5/6843
See application file for complete search history.

(56) References Cited

U.S. PATENT DOCUMENTS 5,033,471 A   7/1991  Yokoe et al.
5,439,002 A   8/1995  Narimatsu et al.
(Continued)

FOREIGN PATENT DOCUMENTS

CN   1320411 A   11/2001
CN   1440722 A   9/2003
(Continued)

OTHER PUBLICATIONS

International Search Report issued in corresponding Application No. PCT/JP2015/078538, dated Dec. 28, 2015 (3 pages).
(Continued)

*Primary Examiner* — Puya Agahi
(74) *Attorney, Agent, or Firm* — Osha Bergman Watanabe & Burton LLP

(57) ABSTRACT

A blood pressure measurement device is equipped with a pressing surface which is formed with pressure sensors, an air bag for pressing the pressing surface toward a radius artery that runs under a skin of a living body; an air bag drive unit for controlling the pressing force of the air bag, and a control unit for calculating blood pressure values in the radius artery on the basis of pressure pulse waves that were detected by all of the pressure sensors in a process that the pressing force was increased or decreased.

10 Claims, 16 Drawing Sheets

(51) Int. Cl.
  *A61B 5/021* (2006.01)
  *A61B 5/02* (2006.01)
(52) U.S. Cl.
  CPC .......... *A61B 5/6843* (2013.01); *A61B 5/7278* (2013.01); *A61B 5/02* (2013.01); *A61B 5/021* (2013.01); *A61B 5/02225* (2013.01); *A61B 2560/0223* (2013.01); *A61B 2560/0238* (2013.01); *A61B 2562/04* (2013.01)

(56) References Cited

U.S. PATENT DOCUMENTS

| | | |
|---|---|---|
| 6,394,959 B1 | 5/2002 | Takaya |
| 2003/0181816 A1 | 9/2003 | Shirasaki |
| 2010/0286538 A1 | 11/2010 | Kim et al. |
| 2012/0316448 A1 | 12/2012 | Gu et al. |

FOREIGN PATENT DOCUMENTS

| | | |
|---|---|---|
| CN | 1524490 A | 9/2004 |
| CN | 1849998 A | 10/2006 |
| CN | 102178518 A | 9/2011 |
| CN | 102613966 A | 8/2012 |
| CN | 102985000 A | 3/2013 |
| CN | 103354729 A | 10/2013 |
| EP | 0852126 A2 | 7/1998 |
| JP | H1-242031 A | 9/1989 |
| JP | H2-261421 A | 10/1990 |
| JP | H7-124130 A | 5/1995 |
| JP | H08187230 A | 7/1996 |
| JP | H11-9562 A | 1/1999 |
| JP | 2004-113368 A | 4/2004 |
| WO | 2001/85024 A1 | 11/2001 |

OTHER PUBLICATIONS

Written Opinion issued in corresponding Application No. PCT/JP2015/078538, dated Dec. 28, 2015 (3 pages).

Search Report issued in European Application No. 15854593.9, dated Apr. 6, 2018 (8 pages).

Office Action in counterpart Chinese Application No. 201580058702.8 dated Jun. 4, 2019 (16 pages).

Office Action issued in corresponding Chinese Application No. 201580058702.8; dated Jul. 2, 2020 (26 pages).

BLOOD PRESSURE MEASUREMENT DEVICE

CROSS-REFERENCE TO RELATED APPLICATION(S)

This is a Continuation Application of PCT Application No. PCT/JP15/078538, filed on Oct. 7, 2015, which was published under PCT Article 21(2) in Japanese. The present application is based on Japanese Patent Application No. 2014-223249 filed on Oct. 31, 2014, the entire contents of which are incorporated herein by reference.

TECHNICAL FIELD

The present invention relates to a blood pressure measurement device.

BACKGROUND ART

Living body information measurement devices are known which can measure living body information such as a pulse rate and a blood pressure using information that is detected by a pressure sensor in a state that the pressure sensor is in direct contact with a living body part where an artery such as a wrist radius artery runs (refer to JP-2004-113368-A, JP-H02-261421-A, JP-H07-124130-A and JP-H01-242031-A, for example).

In the blood pressure measurement device disclosed in JP-2004-113368-A, blood pressure values in a part that is different from a living body part to which a pressure sensor is brought into contact are calculated using a cuff and calibration data is generated using the calculated blood pressure values. Blood pressure values are calculated for each beat by calibrating a pressure pulse wave detected by the pressure sensor using the calibration data.

JP-H02-261421-A, JP-H07-124130-A and JP-H01-242031-A disclose blood pressure measurement devices which measure a blood pressure for each beat without using a cuff, that is, using only information detected by a pressure sensor that is set in contact with a wrist.

As disclosed in JP-H02-261421-A, JP-H07-124130-A and JP-H01-242031-A, measuring a blood pressure using only information detected by the pressure sensor that is set in contact with a living body makes it possible to miniaturize the device. The devices disclosed in JP-H02-261421-A and JP-H07-124130-A are such that a blood pressure is calculated by calibrating or correcting a pressure pulse wave that is detected by the pressure sensor in a state that the pressure sensor is pressed by an optimum pressing force.

To determine the optimum pressing force, it is necessary to execute a process in which the pressing force of the pressure sensor is varied continuously. A blood pressure calculation is enabled only after this process is finished and a state that the pressing force of the pressure sensor is controlled to an optimum pressing force is established.

As a result, in these devices, it is necessary to execute processes of pressing the pressure sensor against a living body part, canceling the pressing, and pressing the pressure sensor in such a manner that its pressing force is set equal to the optimum pressing force. Repetition of these processes is troublesome to the user.

On the other hand, in the device disclosed in JP-H01-242031-A, blood pressure values can be calculated on the basis of a variation of the amplitude of a pressure pulse wave that is detected in a process that the pressing force of the pressure sensor is varied continuously. As a result, a blood pressure can be measured in a short time without causing a user to feel troublesome.

However, in the process that the pressing force of the pressure sensor is varied continuously, the position of the artery being pressed may vary. In the method disclosed in JP-H01-242031-A, such a variation may disable an accurate measurement of a blood pressure.

SUMMARY

One object of the invention is therefore to provide a blood pressure measurement device capable of measuring a blood pressure with high accuracy in a short time without causing a user to feel troublesome.

A blood pressure measurement device according to the invention comprises at least one element array of plural pressure detecting elements arranged in one direction; a pressing unit which presses the element array against a skin of a living body toward an artery in a state that the one direction crosses a direction in which the artery runs; a pressing control unit which controls a pressing force of the pressing unit; and a first blood pressure calculation unit which calculates first blood pressure values in the artery on the basis of pressure pulse waves that were detected by the respective pressure detecting elements included in the element array in a process that the pressing force was increased or decreased by a control of the pressing control unit, wherein first blood pressure calculation unit performs processing of selecting at least one of the pressure detecting elements included in the element array at each of plural time points in a process that the pressing force is increased or decreased on the basis of pressure pulse waves that were detected by the respective pressure detecting elements included in the element array at each of the plural time points, and calculates first blood pressure values in the artery on the basis of first pressure pulse waves that were detected at the plural time points by the pressure detecting elements selected through the processing of selecting performed at the plural time points, respectively.

The invention can provide a blood pressure measurement device capable of measuring a blood pressure with high accuracy in a short time without causing a user to feel troublesome.

DETAILED DESCRIPTION

An embodiment of the present invention will be hereinafter described with reference to the drawings.

Figure 1:
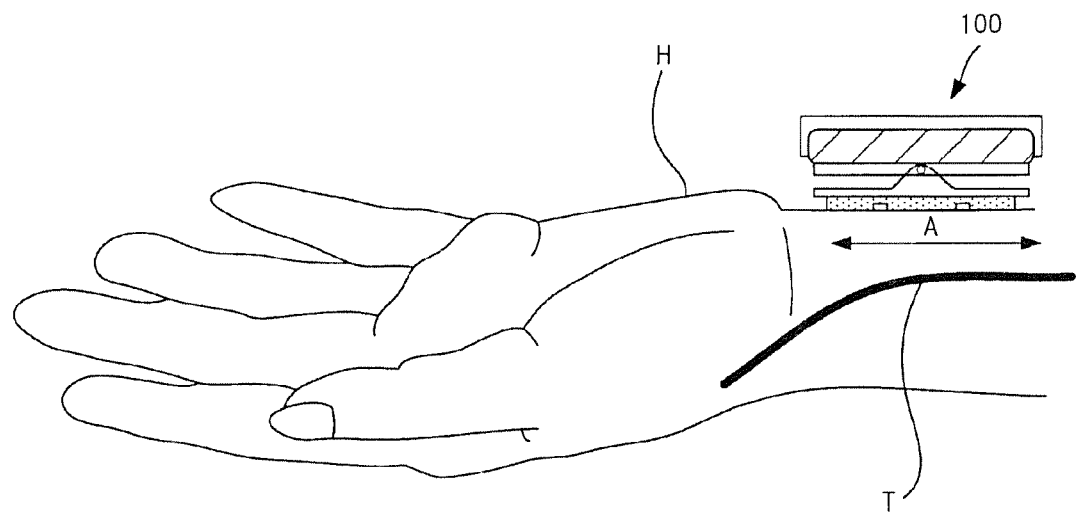
FIG. 1 is an appearance view showing, for description of one embodiment of the invention, the configuration of a pressure pulse wave detection unit 100 of a blood pressure measurement device.

FIG. 1 is an appearance view showing, for description of one embodiment of the invention, the configuration of a pressure pulse wave detection unit 100 of a blood pressure measurement device. The blood pressure measurement device according to the embodiment can be attached, by a belt (not shown), to a living body part (in the example of FIG. 1, a wrist of a user H) inside of which an artery (in the example of FIG. 1, a radius artery T) as a blood pressure measurement target runs.

Figure 2:
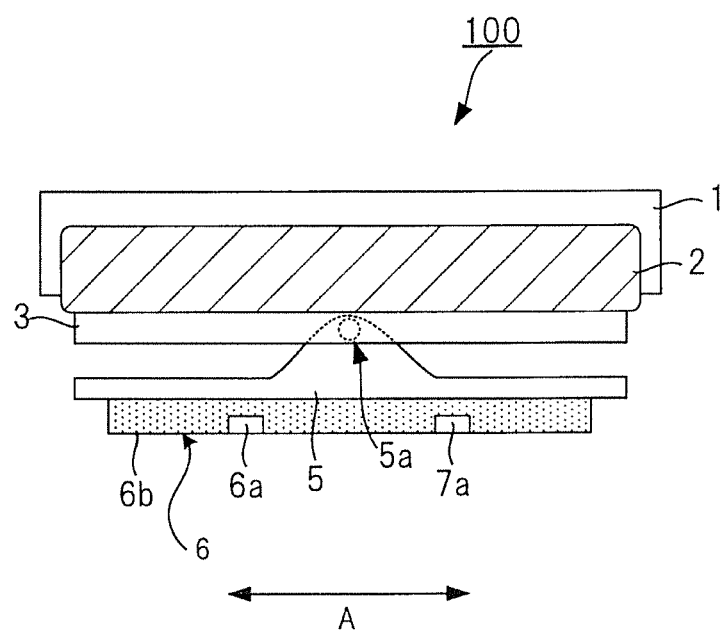
FIG. 2 is an enlarged view of the pressure pulse wave detection unit 100 shown in FIG. 1.
Figure 3:
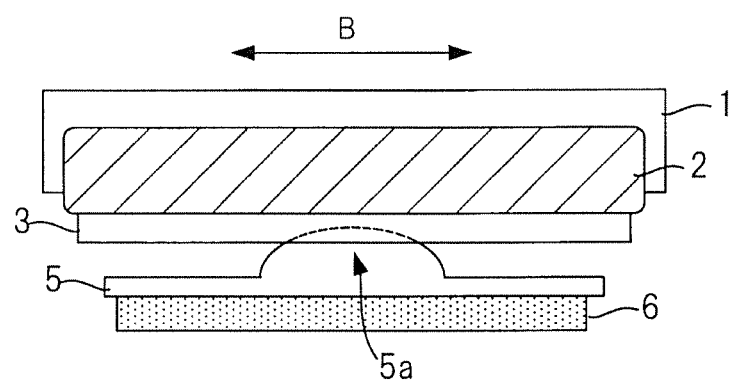
FIG. 3 is a view, as viewed from the side of the fingertips of a user, of the pressure pulse wave detection unit 100 shown in FIG. 1 that is in an attached state.
Figure 4:
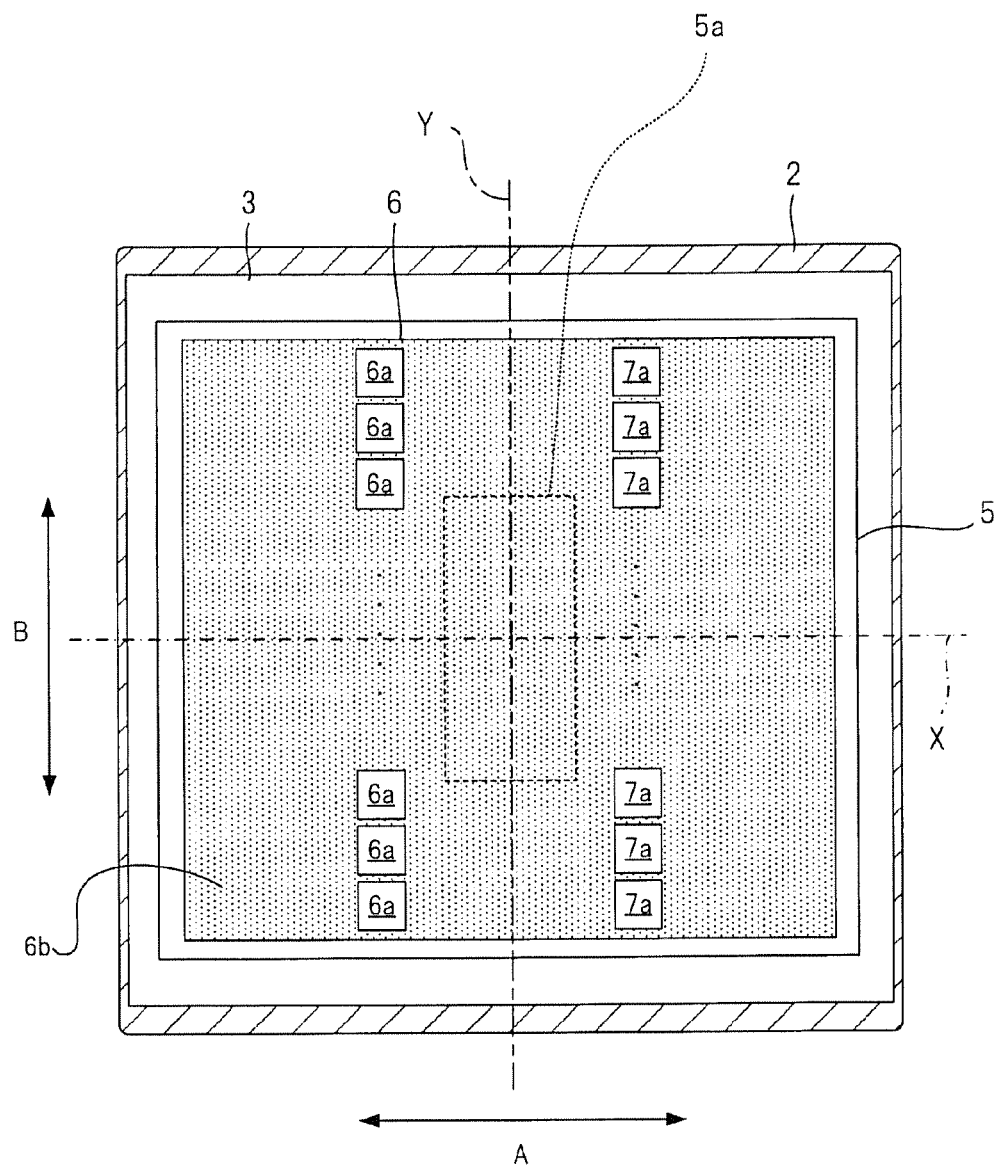
FIG. 4 is a view, as viewed from the side of the part being in contact with the wrist, of the pressure pulse wave detection unit 100 shown in FIG. 1 that is in an attached state.

FIG. 2 is an enlarged view of the pressure pulse wave detection unit 100 shown in FIG. 1. FIG. 3 is a view, as viewed from the side of the fingertips of the user H, of the pressure pulse wave detection unit 100 shown in FIG. 1 that is in an attached state. FIG. 4 is a view, as viewed from the side of the part being in contact with the wrist, of the pressure pulse wave detection unit 100 shown in FIG. 1 that is in an attached state. FIGS. 1 to 4 are schematic views of pressure pulse wave detection unit 100 and should not be construed as restricting the dimensions of individual portions, their arrangement, and other things.

The pressure pulse wave detection unit 100 is equipped with a body 1 which incorporates an air bag 2, a flat plate member 3 which is fixed to the air bag 2, a rotary member 5 which is supported by a biaxial rotating mechanism 5a so as to be rotatable about each of two axes relative to the flat plate member 3, and a sensor unit 6 which is attached to a flat surface, opposite to the flat plate member 3, of the rotary member 5.

As shown in FIG. 1, the air bag 2 functions as a pressing unit for pressing a pressing surface 6b of the sensor unit 6 against an artery that is located under the skin of a living body part (wrist) in a state that the blood pressure measurement device is attached to the wrist. The pressing unit may be any kind of unit as long as it can press the pressing surface 6b of the sensor unit 6 toward an artery; it is not limited to units that employ an air bag.

The amount of air existing inside the air bag 2 is controlled by a pump (not shown), whereby the air bag 2 moves the flat plate member 3 which is fixed to the air bag 2 in the direction that is perpendicular to a surface (a flat surface located on the rotary member 5 side) of the flat plate member 3.

In the attached state shown in FIG. 1, the pressing surface 6b of the sensor unit 6 which is included in the pressure pulse wave detection unit 100 is in contact with the skin of the wrist of the user. When the amount of air injected in the air bag 2 is increased in this state, the internal pressure of the air bag 2 is increased, whereby the sensor unit 6 is pushed toward a radius artery T that exists in the wrist. The following description will be made with an assumption that the pressure force that is exerted toward the radius artery T by the sensor unit 6 is equivalent to the internal pressure of the air bag 2.

As shown in FIG. 4, the pressing surface 6b is formed with plural pressure sensors 6a (pressure detecting elements) which are arranged in a direction B (one direction) that crosses (in the example of FIG. 1, is perpendicular to) a direction A in which the radius artery T extends that exists in the attachment target part, in the attached state shown in FIG. 1. The pressing surface 6b is also formed with plural pressure sensors 7a which are arranged in the direction B. Each pressure sensor 6a and a pressure sensor 7a that is located at the same position as the pressure sensor 6a in the direction B constitute a pair, and plural such pairs are arranged in the direction B on the pressing surface 6b. The pressure sensors (plural pressure sensors 6a and plural pressure sensors 7a) included in the pressure pulse wave detection unit 100 constitute a pressure detection unit.

The pressing surface 6b is a surface of a semiconductor substrate which is made of, for example, single crystal silicon and the pressure sensors 6a and 7a are, for example, pressure-sensitive diodes formed on the surface of the semiconductor substrate.

The pressure sensors 6a (7a) are pressed against the radius artery T in such a manner that its arrangement direction crosses (is approximately perpendicular to) the radius artery T, and the pressure sensors 6a detect a pressure vibration wave (i.e., pressure pulse wave) that is generated from the radius artery T and transmitted to the skin.

The interval between the pressure sensors 6a (7a) is set sufficiently small so that a necessary and sufficient number of pressure sensors 6a (7a) are arranged over the radius artery T. The arrangement length of the pressure sensors 6a (7a) is set necessarily and sufficiently greater than the diameter of the radius artery T.

As shown in FIG. 4, the biaxial rotating mechanism 5a is a mechanism for rotating the rotary member 5 about each of two rotation axes X and Y which are perpendicular to the direction in which the flat plate member 3 is pushed by the air bag 2.

The biaxial rotating mechanism 5a has the two orthogonal rotation axes X and Y which are set on the surface of the flat plate member 3 and about each of which rotational driving is performed by a rotational drive unit 10 (described later).

The rotation axis Y is a first axis that extends in the arrangement direction of the plural pressure sensors 6a (7a) formed on the pressing surface 6b. As shown in FIG. 4 (plan view), the rotation axis Y is set between (in the example of FIG. 4, at the center of) the element array of the plural pressure sensors 6a and the element array of the plural pressure sensors 7a.

The rotation axis X is a second axis that extends in the direction that is perpendicular to the arrangement direction of the plural pressure sensors 6a (7a) formed on the pressing surface 6b. In the example of FIG. 4, the rotation axis X is set as a straight line that equally divides each of the element array of the plural pressure sensors 6a and the element array of the plural pressure sensors 7a.

When the rotary member 5 is rotated about the rotation axis X, the pressing surface 6b is rotated about the rotation axis X. When the rotary member 5 is rotated about the rotation axis Y, the pressing surface 6b is rotated about the rotation axis Y.

Figure 5:
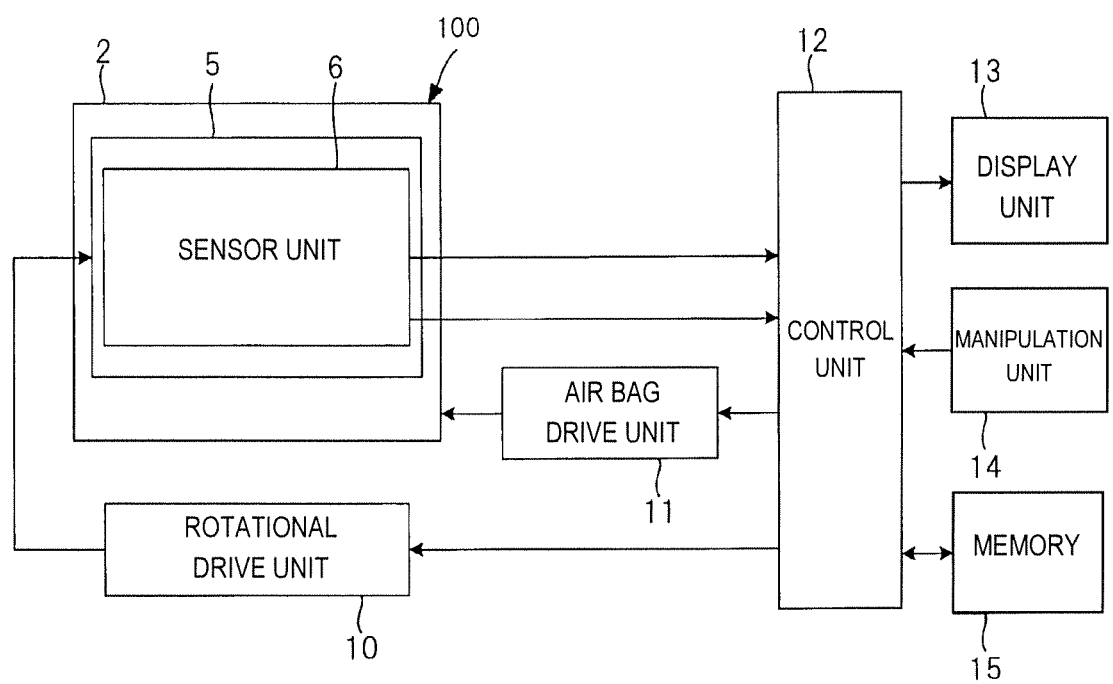
FIG. 5 is a diagram for showing a block configuration of the blood pressure measurement device other than the pressure pulse wave detection unit 100.

FIG. 5 is a diagram for showing a block configuration of the blood pressure measurement device other than the pressure pulse wave detection unit 100.

The blood pressure measurement device is equipped with the pressure pulse wave detection unit 100, a rotational drive unit 10, an air bag drive unit 11, a control unit 12 for centralized control of the entire device, a display unit 13, a manipulation unit 14, and a memory 15.

The rotational drive unit 10 is an actuator that is connected to each of the rotation axes (shafts) X and Y of the biaxial rotating mechanism 5a of the pressure pulse wave detection unit 100. The rotational drive unit 10 rotates the pressing surface 6b about the rotation axes X and Y by rotationally driving the rotation axes (shafts) X and Y individually according to an instruction from the control unit 12.

The air bag drive unit 11 controls the amount of air to be injected in the air bag 2 according to an instruction from the control unit 12.

The display unit 13, which uses, for example, a liquid crystal, serves to display various kinds of information such as measured blood pressure values.

The manipulation unit 14, which is an interface for input of an instruction signal for the control unit 12, is composed of buttons for commanding a start of any of various operations including a blood pressure measurement and other components.

The memory 15 includes a ROM (read-only memory) for storing programs and data for allowing the control unit 12 to perform prescribed operations, a RAM (random access memory) as a working memory, a flash memory for storing various kinds of information such as measured blood pressure data, and other components.

The control unit 12 functions as a pressing control unit, a first blood pressure calculation unit, a rotation control unit, a second blood pressure calculation unit, a calibration data generation unit, a judging unit, and a processing unit by running the programs stored in the ROM of the memory 15.

The pressing control unit controls the pressing force that the pressing surface 6b exerts on the wrist by adjusting the amount of air that occupies the inside the air bag 2 by controlling the air bag drive unit 11.

The first blood pressure calculation unit calculates first blood pressure values in the radius artery T on the basis of pressure pulse waves that are detected by the pressure sensors 6a and 7a formed in the pressing surface 6b in a state that the pressing surface 6b is pressed toward the radius artery T.

More specifically, the first blood pressure calculation unit calculates first blood pressure values in the radius artery T on the basis of pressure pulse waves that were detected by the pressure sensors 6a and 7a in a process that the pressing force acting on the radius artery T was varied (increased or decreased) by the air bag drive unit 11.

The calibration data generation unit generates calibration data using the first blood pressure values calculated by the first blood pressure calculation unit.

The rotation control unit judges whether it is necessary for the rotational drive unit 10 to rotate the pressing surface 6b, on the basis of pressure pulse waves that were detected by the pressure sensors 6a and 7a in a process that the pressing force acting on the radius artery T was increased by the air bag drive unit 11. If judging that rotation is necessary, the rotation control unit causes the rotational drive unit 10 to rotate the pressing surface 6b.

The second blood pressure calculation unit calculates second blood pressure values in the radius artery T by calibrating, using the calibration data, a pressure pulse wave that is detected by the pressure sensors 6a and 7a for each beat in a state that the pressing surface 6b is pressed toward the radius artery T with an optimum pressing force for deforming part of the radius artery T into a flat shape.

The judging unit judges whether detection conditions of a pressure pulse wave as a target of calibration using the calibration data coincides with detection conditions of a pressure pulse wave that was used for generation of the calibration data.

The processing unit performs processing depending on a judgment result of the judging unit.

A description will be made below of how the blood pressure measurement device according to the embodiment operates. The blood pressure measurement device according to the embodiment has a continuous blood pressure measurement mode in which a blood pressure value SBP (systolic blood pressure) what is called a maximum blood pressure and a blood pressure value DBP (diastolic blood pressure) what is called a minimum blood pressure are measured and displayed on the display unit 13 beat by beat.

Figure 6:
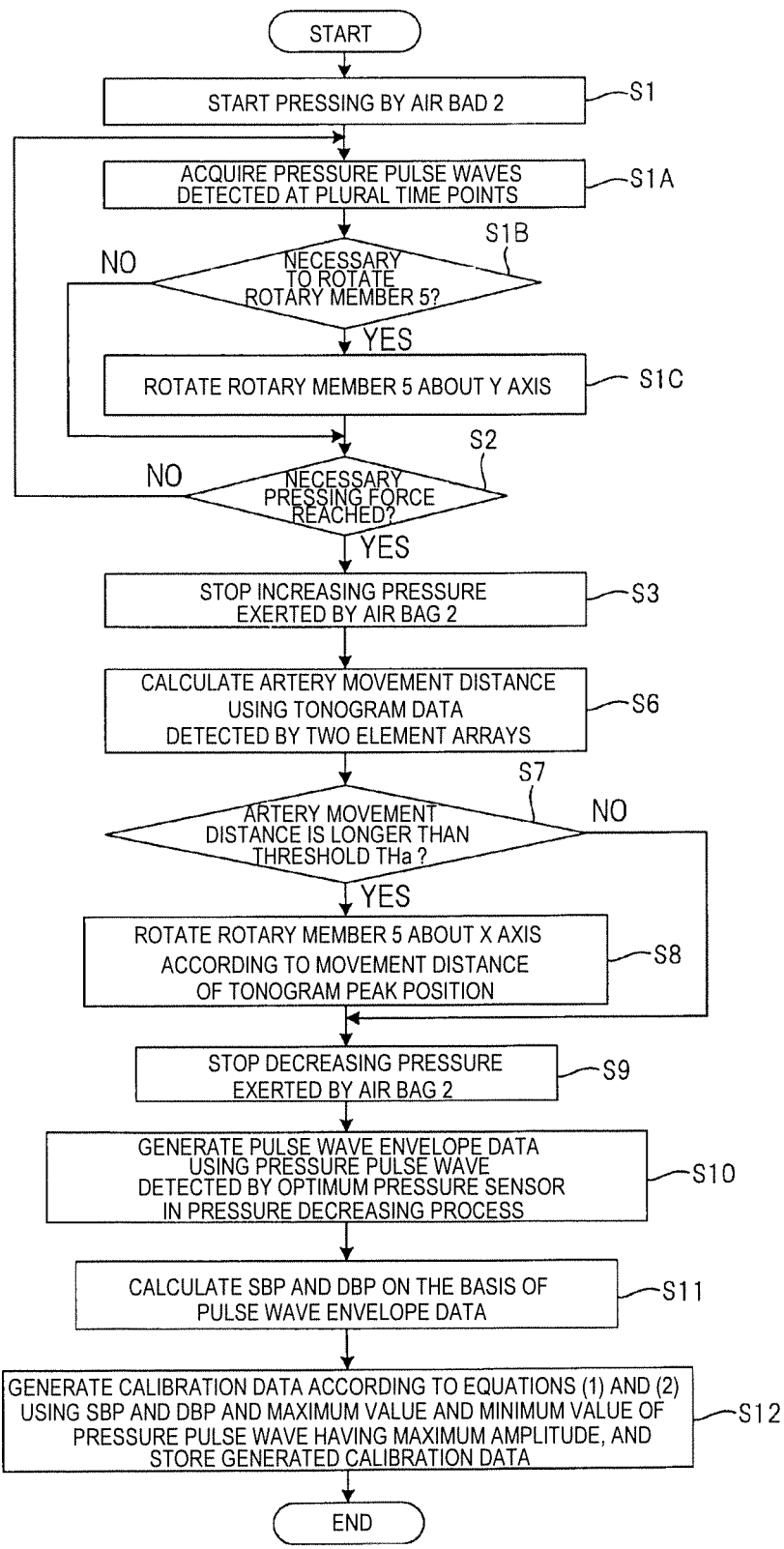
FIG. 6 is a flowchart for illustrating an operation, to generation of calibration data in a continuous blood pressure measurement mode, of the pressure measurement device according to the embodiment.

FIG. 6 is a flowchart for illustrating an operation, to generation of calibration data in the continuous blood pressure measurement mode, of the pressure measurement device according to the embodiment.

It is assumed that in an initial state, that is, a state before reception of a blood pressure measurement instruction, the rotation amount of the rotary member 5 of the pressure pulse wave detection unit 100 is set at, for example, zero, that is, the pressing surface 6b is parallel with the flat plate member 3.

Although the state that the rotation amount is set at zero is employed here as the initial state, the invention is not limited this case. For example, the initial state may be a state that the rotational drive unit 10 has rotated the pressing surface 6b so that the pressing surface 6b comes into uniform contact with the skin according to the shape of the wrist to which the blood pressure measurement device is attached.

Upon reception of a blood pressure measurement instruction, the control unit 12 controls the air bag drive unit 11 to start injecting air into the air bag 2 and thereby increases the pressing force that the pressing surface 6b exerts toward the radius artery T (step S1).

In the process of increasing the pressing force, with certain timing (e.g., periodic timing) after a lapse of a sufficient time from a start of closure of the radius artery T, the control unit 12 acquires plural latest pressure pulse wave information I1 (pressure pulse waves) that have been detected by the respective pressure sensors 6a so far and are stored in the memory 15. With the certain timing, the control unit 12 acquires plural latest pressure pulse wave information I2 (pressure pulse waves) that have been detected by the respective pressure sensors 7a so far and are stored in the memory 15 (step S1A).

The control unit 12 calculates, for example, an amplitude average value Ave1 of pressure pulse waves that were detected by the respective pressure sensors 6a at time t1 among the plural pressure pulse wave information I1 acquired at step 1A and an amplitude average value Ave2 of pressure pulse waves that were detected by the respective pressure sensors 6a at time t2 that is later than time t1. The control unit 12 also calculates an amplitude average value Ave3 of pressure pulse waves that were detected by the respective pressure sensors 7a at time t1 among the plural pressure pulse wave information I2 acquired at step 1A and an amplitude average value Ave4 of pressure pulse waves that were detected by the respective pressure sensors 7a at time t2. Then the control unit 12 calculates ratios between the average values calculated at the same time points, that is, Ave1/Ave3 and Ave2/Ave4.

The control unit 12 judges whether to cause the rotational drive unit 10 to rotate the rotary member 5 on the basis of a variation between the ratios calculated the plural time points. That is, the control unit 12 judges whether to rotate the rotary member 5 on the basis of the pressure pulse waves detected by the pressure sensors 6a and 7a at the plural time points in the process that the pressing force is increased (step S1B).

For example, if the ratios calculated at the plural time points show monotonic increase, it can be judged that the element array of the pressure sensors 7a are located on the side on which the radius artery T is closed and the element array of the pressure sensors 6a are not located on that side. Thus, the control unit 12 judges that it is necessary to rotate the rotary member 5.

If the ratios calculated at the plural time points show monotonic decrease, it can be judged that the element array of the pressure sensors 6a are located on the side on which the radius artery T is closed and the element array of the pressure sensors 7a are not located on that side. Thus, the control unit 12 judges that it is necessary to rotate the rotary member 5.

If the ratios calculated at the plural time points show almost no variation, it can be judged that the two element arrays are detecting pressure pulse waves of the radius artery T in the same manner. Thus, the control unit 12 judges that it is not necessary to rotate the rotary member 5.

If the ratios calculated at plural time points show increase and decrease repeatedly, it cannot be judged whether the radius artery T is pressed sufficiently on the respective sides of the two element arrays or the radius artery T is not pressed sufficiently only on the side of one element array. Thus, the control unit 12 judges that it is not necessary to rotate the rotary member 5.

As described above, the control unit 12 judges whether rotation is necessary on the basis of a variation of the ratios calculated at the plural time points. Instead of the ratios, a difference (a sign is taken into consideration) between the average values Ave1 (Ave2) and Ave3 (Ave4) may be used.

Figure 7A:
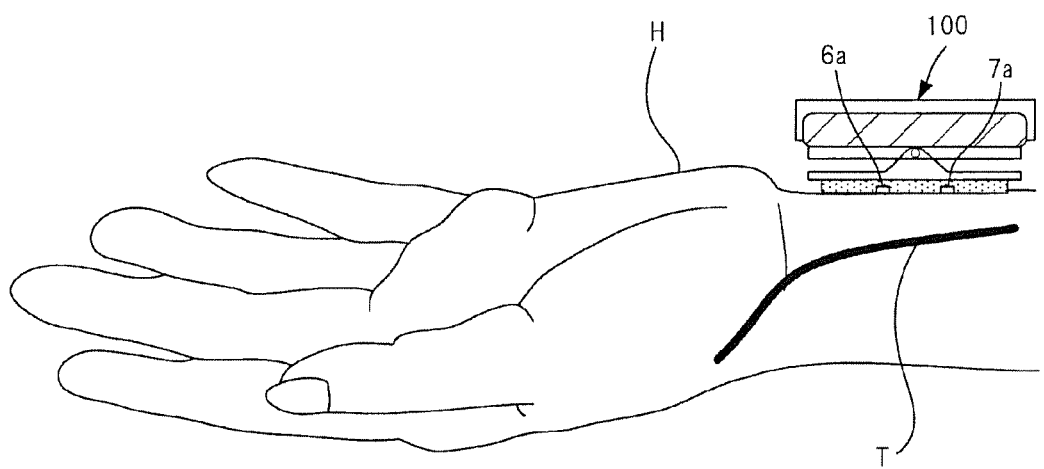
FIGS. 7A and 7B are diagrams for showing an example state that a radius artery is not closed by one of two sensor portions.

FIG. 7A is a diagram for showing an example state that the radius artery T is closed on the side of the element array of the pressure sensors 7a but is not closed on the side of the element array of the pressure sensors 6a. In the state of FIG. 7A, the distance between the element array of the pressure sensors 6a is longer than that between the element array of the pressure sensors 7a.

Let 6A and 7A represent an amplitude average value of pressure pulse waves detected by the respective pressure sensors 6a and an amplitude average value of pressure pulse waves detected by the respective pressure sensors 7a, respectively; then, in the state of FIG. 7A, the ratio 6A/7A is sufficiently larger than 1. In this state, 6A/7A comes closer to 1 if the element array of the pressure sensors 6a is brought closer to the radius artery T (refer to FIG. 7B).

Thus, if judging at step S1B that it is necessary to rotate the rotary member 5 about the rotation axis Y, the control unit 12 performs a control so as to rotate the rotary member 5 about the rotation axis Y according to a 6A/7A value obtained at the latest time point (step S1C).

More specifically, the control unit 12 reads out a rotation amount corresponding to the 6A/7A value by referring to a data table (determined empirically and stored in the memory 15 before shipment of a product) showing a relationship between the 6A/7A value and the rotation amount of the rotary member 5 and sets the read-out rotation amount.

Then, the control unit 12 judges which of the average value 6A and the average value 7A is larger. If the average value 6A is larger, the control unit 12 sets the rotation direction of the rotary member 5 about the rotation axis Y to counterclockwise in FIG. 7 to decrease the distance between the element array of the pressure sensors 6a and the radius artery T.

If the average value 7A is larger, the control unit 12 sets the rotation direction of the rotary member 5 about the rotation axis Y to clockwise in FIG. 7 to decrease the distance between the element array of the pressure sensors 7a and the radius artery T.

Figure 7B:
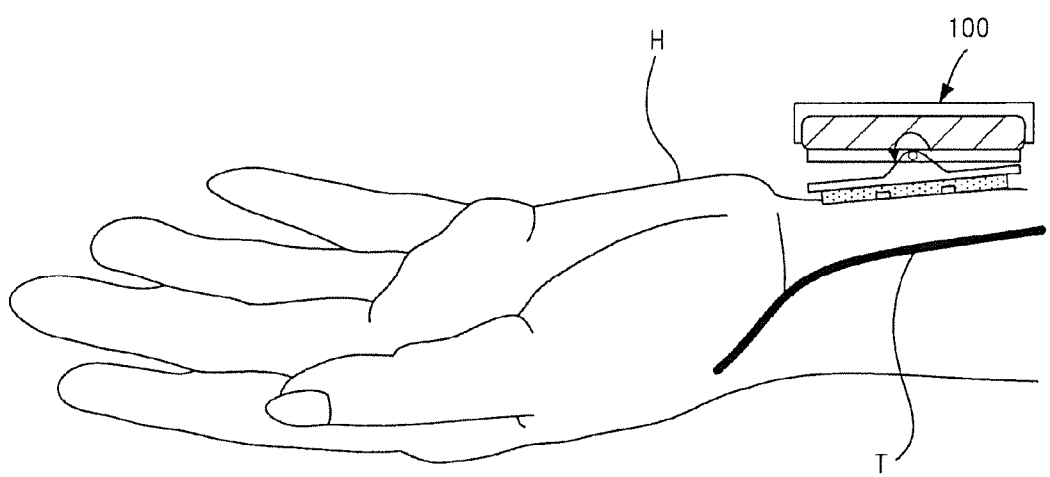

The control unit 12 rotates the rotary member 5 in the thus-set rotation direction by the thus-set rotation amount. As a result, as shown in FIG. 7B, the pressing surface 6b can be made parallel with the radius artery T to establish a state that the radius artery T is closed on the respective sides of the two element arrays.

The control unit 12 moves to step S2 after the execution of step S1C or after the execution of step S1B (if a judgment was made that it is not necessary to rotate the rotary member 5). At step S2, the control unit 12 judges whether the pressing force has become such as to correspond to a pressure that is enough to close the radius artery T (i.e., has reached a necessary pressing force). If judging that the pressing force has reached a necessary pressing force (step S2: yes), the control unit 12 controls the air bag drive unit 11 to stop the injection of air into the air bag 2 (step S3). If judging that the pressing force has not reached a necessary pressing force yet, the control unit 12 returns to step S1A.

After the execution of step S3, the control unit 12 determines an amplitude distribution curve (what is called a tomogram) indicating a relationship between the amplitude of a pressure pulse wave that was detected by each pressure sensor 6a at each time point from step S1 to step S3 and the position of the pressure sensor 6a in the pressing surface 6b. The control unit 12 also determines a tomogram indicating a relationship between the amplitude of a pressure pulse wave that was detected by each pressure sensor 7a at each time point and the position of the pressure sensor 7a in the pressing surface 6b.

The control unit 12 stores the tomogram generated for the element array of the pressure sensors 6a in the memory 15 in such a manner that it is correlated with identification information of the element array, a detection time of the pressure pulse waves, and a pressing force of the air bag 2 in the pressing direction (an internal pressure of the air bag 2) at the detection time.

Likewise, the control unit 12 stores the tomogram generated for the element array of the pressure sensors 7a in the memory 15 in such a manner that it is correlated with identification information of the element array, a detection time of the pressure pulse waves, and a pressing force of the air bag 2 in the pressing direction at the detection time.

The control unit 12 calculates a movement distance of the radius artery T in the direction B during the pressing of the pressing surface 6b against the wrist using the tomogram data stored in the memory 15 (step S6).

Figure 8A:
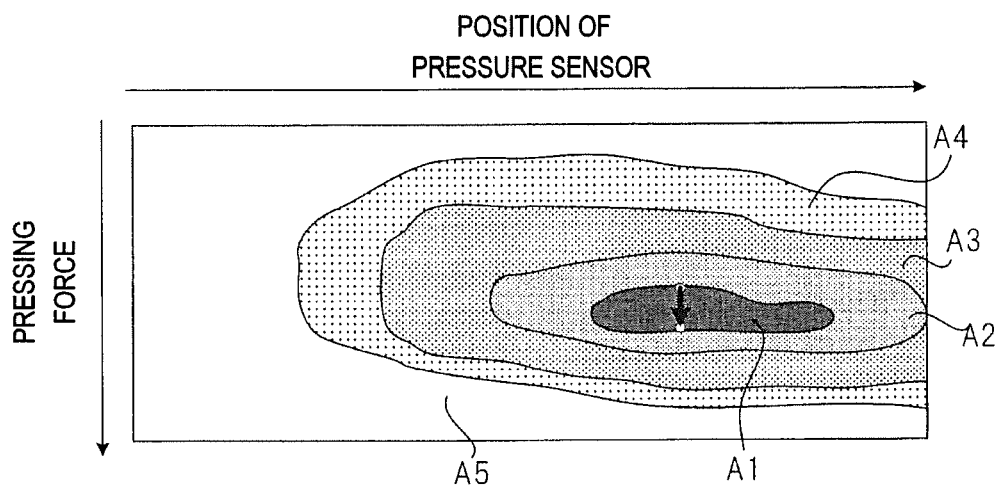
FIGS. 8A and 8B are diagrams for showing examples of amplitude values of pressure pulse waves that are detected by pressure sensors of a sensor unit 6 as the pressing force that the sensor unit 6 exerts on the wrist is varied.
Figure 8B:
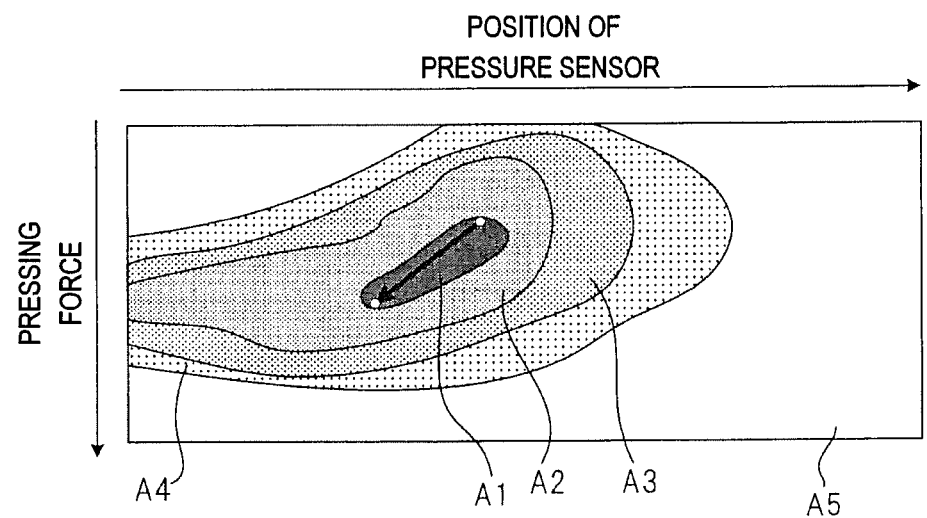

FIGS. 8A and 8B are diagrams for showing examples of amplitude values of pressure pulse waves that are detected by the pressure sensors 6a of the sensor unit 6 as the pressing force that the sensor unit 6 exerts on the wrist is varied. In FIGS. 8A and 8B, the horizontal axis represents the position of the pressure sensor 6a in the direction B and the vertical axis represents the pressing force.

In FIGS. 8A and 8B, the amplitudes of the pressure pulse waves detected by the pressure sensors 6a located at the respective positions are indicated by different colors according to their magnitudes.

Symbol A1 denotes a region where the amplitude is larger than or equal to a threshold TH1. Symbol A2 denotes a region where the amplitude is larger than or equal to a threshold TH2 and smaller than the threshold TH1. Symbol A3 denotes a region where the amplitude is larger than or equal to a threshold TH3 and smaller than the threshold TH2. Symbol A4 denotes a region where the amplitude is larger than or equal to a threshold TH4 and smaller than the threshold TH3. Symbol A5 denotes a region where the amplitude is smaller than the threshold TH4. There is a relationship that (threshold TH1)>(threshold TH2)>(threshold TH3)>(threshold TH4).

The example of FIG. 8A is such that the positions of pressure sensors 6a that detect pressure pulse waves whose amplitudes are larger than or equal to the threshold TH1 have almost no changes in a process that the pressing force is increased. In contrast, the example of FIG. 8B is such that the positions of pressure sensors 6a that detect pressure pulse waves whose amplitudes are larger than or equal to the threshold TH1 shift leftward in a process that the pressing force is increased.

Figure 9A:
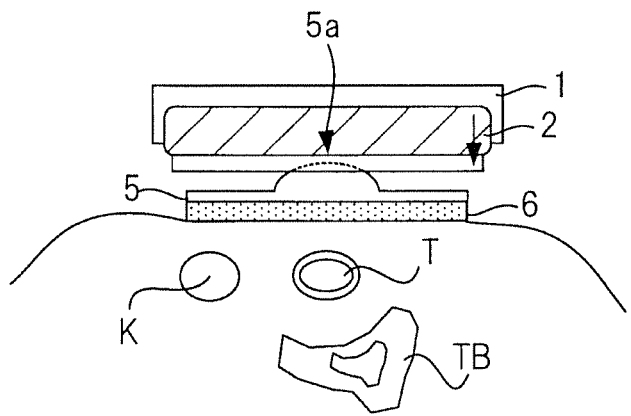
FIGS. 9A to 9C are diagrams for showing how pressing of the sensor unit 6 against the wrist by an air bag 2 proceeds after attachment of the pressure pulse wave detection unit 100 to the wrist.
Figure 9B:
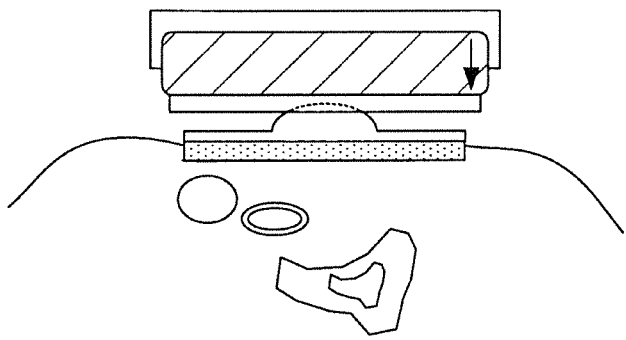
Figure 9C:
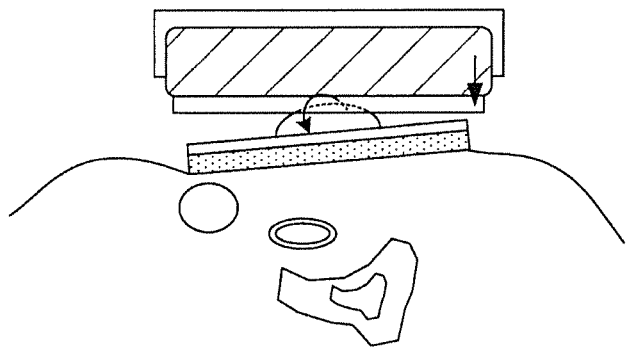

FIGS. 9A to 9C are diagrams for showing how pressing of the sensor unit 6 against the wrist by the air bag 2 proceeds after attachment of the pressure pulse wave detection unit 100 to the wrist. In FIGS. 9A to 9C, symbol TB denotes the radius and symbol K denotes a tendon.

After pressing of the sensor unit 6 against the wrist by the air bag 2 is started as shown in FIG. 9A, there may occur an event that the radius artery T is moved in the direction B as shown in FIG. 9B.

If the radius artery T is moved in the direction B as shown in FIG. 9B during pressing, the distribution of the amplitude values of pressure pulse waves vary as shown in FIG. 8B during the pressing. More specifically, there occurs a large difference between the position of a pressure sensor 6a that detects an amplitude value that is larger than or equal to the threshold TH1 first as the pressing force is increased and the position of a pressure sensor 6a that detects an amplitude value that is larger than or equal to the threshold TH1 last.

In the example of FIG. 8A, there is no large difference between the position of a pressure sensor 6a that detects an amplitude value that is larger than or equal to the threshold TH1 first as the pressing force is increased and the position of a pressure sensor 6a that detects an amplitude value that is larger than or equal to the threshold TH1 last. Thus, it is seen that the radius artery T is closed making almost no movement in the direction B in the process that the pressing force is increased.

In this manner, a position variation of the radius artery T in the direction B can be detected by checking how the tomogram varies in a process that the pressing force is changed. If the radius artery T is closed by increasing the pressing force while the state of FIG. 9B is left as it is, correct tonograms may not be obtained due to influence from living body tissue such as the tendon K.

In view of the above, at step S6, the control unit 12 calculates a difference (i.e., a movement distance of the radius artery T in the direction B) between the position of a pressure sensor 6a that detected an amplitude value that is larger than or equal to the threshold TH1 first as the pressing force was increased and the position of a pressure sensor 6a that detected an amplitude value that is larger than or equal to the threshold TH1 last on the basis of data as shown in FIGS. 8A and 8B that indicate a relationship between the pressing force and the tomogram. And the control unit 12 judges whether the calculated difference is larger than or equal to a threshold THa (step S7).

If the difference between the two positions is larger than or equal to the threshold THa (step S7: yes), at step S8 the control unit 12 determines a vector as shown in FIG. 8B by an arrow. If the difference between the two positions is smaller than the threshold THa (step S7: no), the control unit 12 moves to step S9.

Information indicating a relationship between the direction and magnitude of a vector as shown in FIGS. 8A and 8B and the direction and amount of rotation of the rotary member 5 about the rotation axis X is determined empirically and stored in the memory 15 in advance.

The control unit 12 acquires information indicating a rotation direction and amount corresponding to the determined direction and magnitude of the determined vector from the memory 15, and sends the acquired information to the rotational drive unit 10. The rotational drive unit 10 rotates the rotary member 5 according to the received information in the manner shown in FIG. 9C (step S8).

As described above, when receiving a blood pressure measurement instruction, the control unit 12 judges whether it is necessary to rotate the rotary member 5 at steps S1B and S7 on the basis of pressure pulse waves detected by the respective pressure sensors 6a and 7a at plural time points in the process that the pressing force of the air bag 2 was increased. If judging that it is necessary to rotate the rotary member 5 (step S1B: yes; step S7: yes), the rotational drive unit 10 rotates the rotary member 5 on the basis of the pressure pulse waves detected by the respective pressure sensors 6a and 7a.

At step S9 which follows step S8, the control unit 12 starts decreasing the pressing force acting on the radius artery T by discharging air from the air bag 2.

Upon decreasing the pressing force to a minimum value after the reduction of the pressing force was started at step S9, the control unit 12 determines an optimum pressure sensor from among all of the pressure sensors 6a and 7a. For example, the control unit 12 determines, as an optimum pressure sensor, a pressure sensor that detected a pressure pulse wave having a maximum amplitude in the process that the pressing force was decreased.

A pressure pulse wave that is detected by a pressure sensor that is located right over a flat portion of the radius artery T is not affected by tension of the wall of the radius artery T and hence exhibits a maximum amplitude. And this pressure pulse wave provides a highest correlation with the blood pressure inside the radius artery T. For these reasons, a pressure sensor that detected a pressure pulse wave having a maximum amplitude is determined as an optimum pressure sensor.

Plural pressure sensors may be found that detected pressure pulse waves having a maximum amplitude. In this case, it is appropriate to deal with these plural pressure sensors as optimum pressure sensors and to employ an average, for example, of the pressure pulse waves detected by these respective plural pressure sensors as a "pressure pulse wave detected by an optimum pressure sensor."

The control unit 12 generates pulse wave envelope data using the pressure pulse wave detected by the optimum pressure sensor in the pressing force decreasing process (step S10).

The pulse wave envelope data is data that correlates the pressing force (the internal pressure of the air bad 2) that the sensor unit 6 exerts toward the radius artery T and the amplitude of the pressure pulse wave that is detected by the optimum pressure sensor in a state that the optimum pressure sensor is pressed toward the radius artery T by this pressing force.

Figure 10:
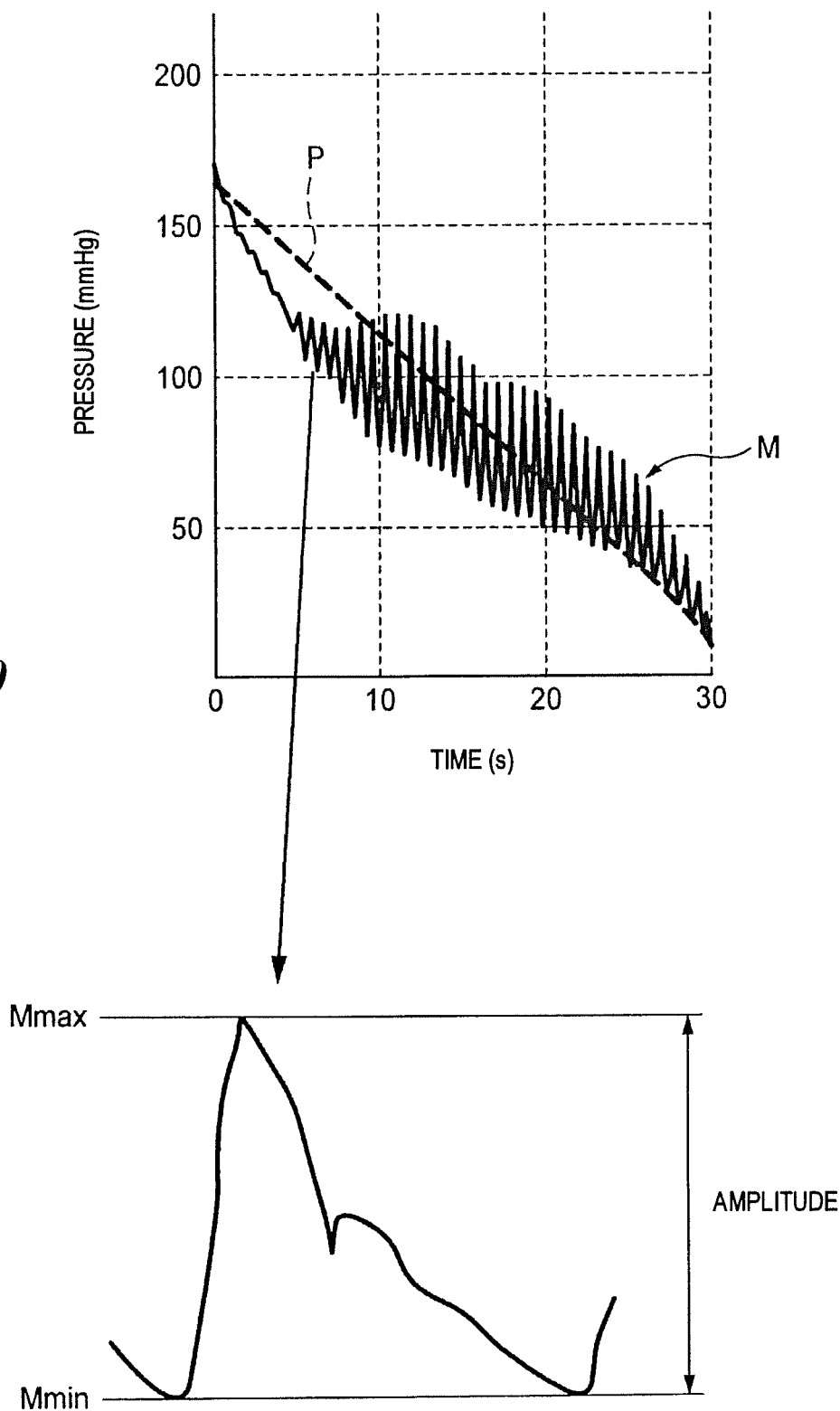
FIG. 10 is a graph for showing an example of how a pressure pulse wave detected by an optimum pressure sensor varies as the pressure acting on the wrist is varied.

FIG. 10 is a graph for showing an example of how a pressure pulse wave detected by an optimum pressure sensor varies as the pressure acting on the wrist is varied. In FIG. 10, a straight line that is given a symbol P indicates the pressure and a waveform that is given a symbol M denotes a pressure wave. An enlarged version of a one-beat pressure pulse wave is shown in a bottom part of FIG. 10.

As shown in FIG. 10, pressures at a rising point and a falling point of each pressure pulse wave are referred to as a minimum value Mmin and a maximum value Mmax, respectively. The amplitude of the pressure pulse wave is a difference between the maximum value Mmax and the minimum value Mmin. Each of the maximum value Mmax and the minimum value Mmin is information characterizing the shape of the pressure pulse wave.

Upon cancellation of a closed state of the radius artery T after a start of reduction of the pressing force, the amplitude of the pressure pulse wave detected by the optimum pressure sensor increases rapidly. The amplitude thereafter varies as shown in FIG. 10 as the pressing force decreases. At step S10, the control unit 12 generates pulse wave envelope data as shown in FIG. 11 on the basis of the relationship between the pressing force and the pressure pulse wave as shown in FIG. 10.

Figure 11:
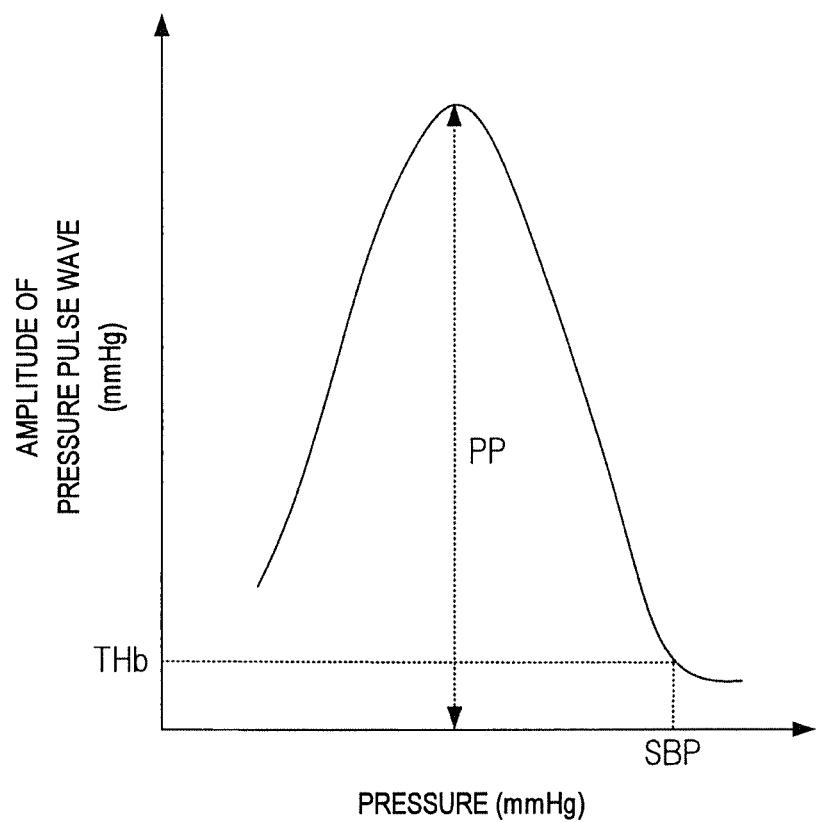
FIG. 11 is a diagram for showing example pulse wave envelope data.

Upon generating the pulse wave envelope data as shown in FIG. 11, the control unit 12 calculates SBP and DBP on the basis of the generated pulse wave envelope data (step S11).

For example, the control unit 12 determines, as SBP, a pressure at a time point when the pressure pulse wave amplitude starts to rise rapidly in the pulse wave envelope shown in FIG. 11 after the start of reduction of the pressing force, that is, a pressure at a time point when the pressure pulse wave amplitude detected by the optimum pressure sensor first exceeds a threshold THb for judgment for an end of an artery closed state after the start of reduction of the pressing force. Alternatively, the control unit 12 calculates a difference between two adjacent amplitude values of the pulse wave envelope data and determines, as SBP, a pressure at a time point when the difference exceeds a threshold.

Furthermore, the control unit 12 employs, as a pulse pressure (PP), a maximum value of the pressure pulse wave amplitude of the pulse wave envelope shown in FIG. 11 and calculates DBP using the calculated SBP and PP according to an equation SBP−DBP=PP.

After the execution of step S11, the control unit 12 generates calibration data to be used in a continuous blood pressure measurement (described later) using a maximum value Mmax and a minimum value Mmin of one (e.g., a pressure pulse wave that had a maximum amplitude) of pressure pulse waves detected by the optimum pressure sensor that was determined in the pressure decreasing process (step S9) and the SBP and DBP calculated at step S11. The control unit 12 stores the generated calibration data in the memory 15 (step S12).

Relationships $$SBP = a \times M\text{max} + b \quad (1)$$

$$DBP = a \times M\text{min} + b \quad (2)$$

holds where a and b are a slope and an intercept of a linear function, respectively.

The control unit 12 calculates the slope a and the intercept b by substituting the SBP and DBP determined at step S11 and the maximum value Mmax and the minimum value Mmin of the pressure pulse wave having a maximum amplitude in the pulse wave envelope shown in FIG. 11 into Equations (1) and (2). The control unit 12 stores the calculated coefficients a and b and Equations (1) and (2) in the memory 15 as calibration data.

Figure 12:
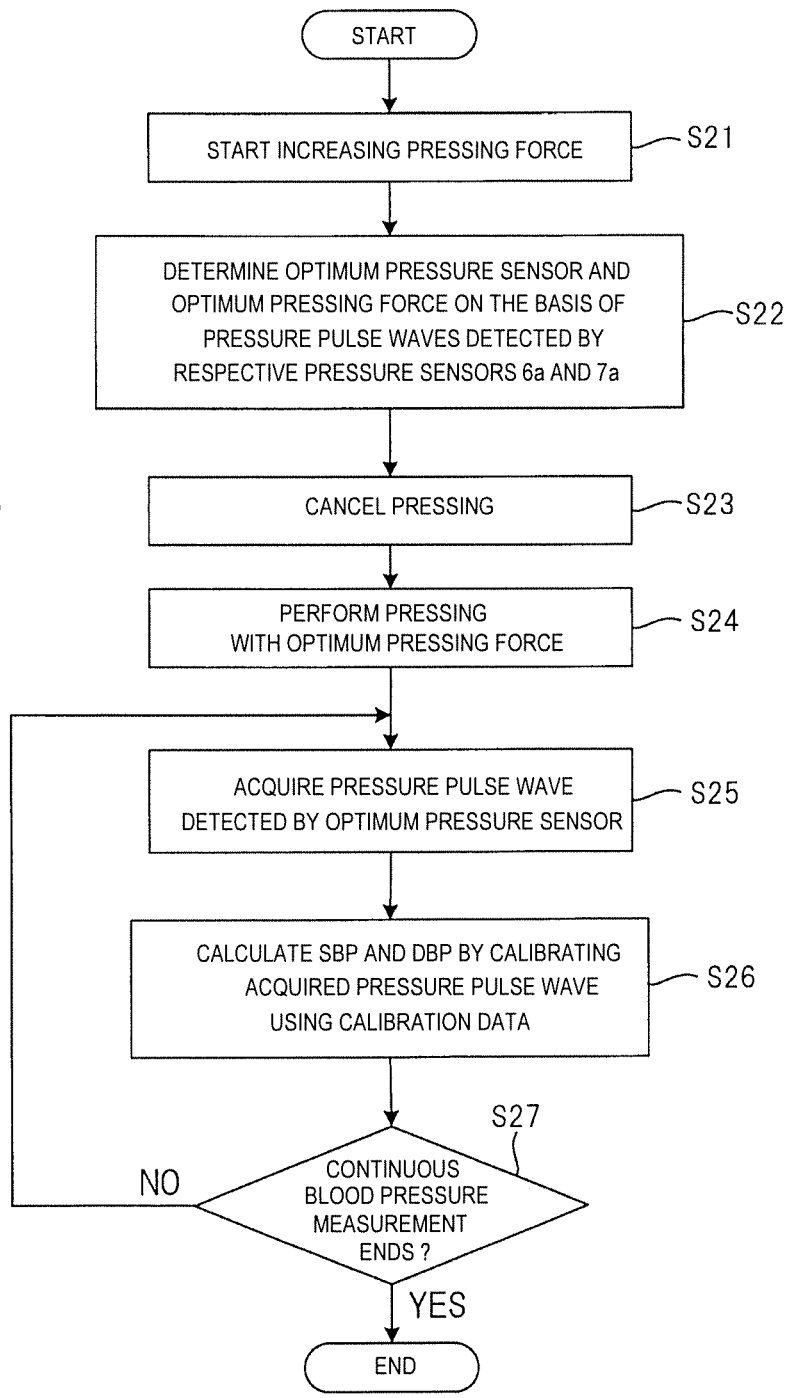
FIG. 12 is a flowchart for illustrating a continuous blood pressure measuring operation in the continuous blood pressure measurement mode of the blood pressure measurement device according to the embodiment.

FIG. 12 is a flowchart for illustrating a continuous blood pressure measuring operation in a continuous blood pressure measurement mode of the blood pressure measurement device according to the embodiment.

After generating calibration data according to the flowchart shown in FIG. 6, the control unit 12 controls the air bag drive unit 11 to increase the internal pressure of the air bag 2 and thereby increase the pressing force that the pressing surface 6b exerts toward the radius artery T (step S21).

Then the control unit 12 determines, as an optimum pressure sensor, one, that detected a pressure pulse wave having a maximum amplitude, of the pressure sensors 6a and 7a in the process that the pressing force was increased. And the control unit 12 determines, as a pressure corresponding to an optimum pressing force, an internal pressure of the air bag 2 that was produced at a time point of detection of the pressure pulse wave having the maximum amplitude (step S22).

Then the control unit 12 restores the initial state by releasing the air from inside the air bag 2 (step S23). The control unit 12 thereafter increases the internal pressure of the air bag 2 to the pressure corresponding to the optimum pressing force determined at step S22, and maintains the optimum pressing force (step S24).

Subsequently, in a state that the pressing surface 6b is pressed toward the radius artery T with the optimum pressing force, at step S25 the control unit 12 acquires a pressure pulse wave that is detected by the optimum pressure sensor determined at step S22.

Then, at step S26, the control unit 12 calculates SBP and DBP by calibrating the acquired one-beat pressure pulse wave using the calibration data that was generated at step S12 in FIG. 6.

More specifically, the control unit 12 calculates SBP by substituting a maximum value Mmax of the pressure pulse wave acquired at step S25 and the coefficients a and b calculated at step S12 into the above-mentioned Equation (1) and calculates DBP by substituting a minimum pressure value Mmin of the pressure pulse wave acquired at step S25 and coefficients a and b calculated at step S12 into the above-mentioned Equation (2). The control unit 12 causes the display unit 13, for example, to display the calculated SBP and DBP and thereby notifies the user of them.

The control unit 12 finishes the process if receiving an instruction to finish the continuous blood pressure measurement (step S27: yes), and returns to step S25 if not receiving an end instruction (step S27: no).

As described above, the control unit 12 generates calibration data using first blood pressure values that are calculated on the basis of pressure pulse waves that were detected by the sensor unit 6 in a process that the pressing force was decreased. That is, the control unit 12 can calculate blood pressure values mainly on the basis of pressure pulse waves that were acquired in a process that the pressing force was varied irrespective of pressure pulse waves that are detected in a state that the sensor unit 6 is held being pressed with a maximum pressing force. Thus, blood pressures can be calculated without executing the three steps of increasing the internal pressure of the air bag 2, releasing the air from inside the air bag 2, and increasing the internal pressure of the air bag 2 to an optimum pressure.

The blood pressure measurement device according to the embodiment may be provided with a mode in which blood pressures are measured with desired timing and presented to the user. When setting is made to this mode, blood pressures can be measured in a short time and presented to the user without causing the user to feel troublesome by the control unit 12's executing steps S1-S11 shown in FIG. 6.

In the blood pressure measurement device according to the embodiment, data for calibrating a pressure pulse wave detected by a pressure sensor can be generated by only the device that is miniaturized to such an extent as to be attachable to a wrist. This facilitates generation of calibration data for each user even in a case that the blood pressure measurement device is shared by plural users. As a result, each user can start using the device easily even in a case that the device is shared by plural users.

A configuration is possible in which the control unit 12 performs the following operation if in the flowchart of FIG. 6 an affirmative judgment is not made at step S1B even once and a negative judgment is made at step S7, that is, if the rotary member 5 was not rotated during and after a pressing force increasing process.

The control unit 12 determines an optimum pressure sensor (e.g., a pressure sensor that detected a pressure pulse wave having a maximum amplitude) on the basis of pressure pulse waves detected by the respective pressure sensors 6a and 7a in a pressing force increasing process of steps S1-S3. Then the control unit 12 generates pulse wave envelope data using a pressure pulse wave that was detected by the optimum pressure sensor during the pressing force increasing process. The control unit 12 calculates SBP and DBP on the basis of the pulse wave envelope data.

For example, the control unit 12 determines, as SBP, a pressure at a time point when the pressure pulse wave amplitude starts to fall rapidly in the pulse wave envelope after the start of increase of the pressing force, that is, a pressure at a time point when the pressure pulse wave amplitude detected by the optimum pressure sensor first becomes smaller than the threshold THb after the start of increase of the pressing force. A DBP calculation method is the same as used at step S11.

An appropriate action that the control unit 12 is to take after the calculation of the DBP is to generate, by the same method as employed at step S12, calibration data to be used in a continuous blood pressure measurement. More specifically, the control unit 12 generates calibration data using a maximum value Mmax and a minimum value Mmin of, for example, one, having a maximum amplitude, of pressure pulse waves detected by the optimum pressure sensor that was determined in the pressing force increasing process, the calculated SBP and DBP, and Equations (1) and (2). The control unit 12 stores the generated calibration data in the memory 15.

In this case, the control unit 12 determines, as an optimum pressure sensor, a sensor that detected a pressure pulse wave having a maximum amplitude in the pressing force increasing process of steps S1-S3 shown in FIG. 6. Thus, after generating the calibration data, the control unit 12 determines, as a pressure corresponding to an optimum pressing force, an internal pressure of the air bag 2 at the time point of detection of the pressure pulse wave having the maximum amplitude instead of executing steps S21-S23, controls the internal pressure of the air bag 2 to the pressure corresponding to the optimum pressing force at step S24, and thereafter executes step S25 and the following steps shown in FIG. 12.

As described above, it is possible to generate pulse wave envelope data using pressure pulse waves that are detected in a process that the pressing force acting on the radius artery T is increased and to calculate SBP and DBP on the basis of this pulse wave envelope data.

The situation that an affirmative judgment is not made at step S1B even once and a negative judgment is made at step S7 occurs in a case that the pressing against the radius artery T is being made in a form that is close to an ideal form. Thus, in this case, since SBP and DBP are calculated using pressure pulse waves that have already been acquired in a pressing force increasing process, the time required for a blood pressure calculation can be shortened.

Where a calibration blood pressure is calculated on the basis of pressure pulse waves acquired in a pressing force increasing process, it is not necessary to determine an optimum pressure sensor or an optimum pressing force again in a continuous blood pressure measurement. This makes it possible to shorten the time to completion of a first-beat blood pressure measurement as well as to reduce the power consumption.

Where as described above the device is provided with the mode in which blood pressures are measured with desired timing and presented to the user, if the control unit 12 judges that rotation of the rotary member 5 is not necessary (i.e., an affirmative judgment is not made at step S1B even once and a negative judgment is made at step S7) because no large variation has occurred in the position of the radius artery T, a blood pressure measurement can be completed only by two steps, that is, a step of increasing the pressing force for pressing the pressure sensors to the living body part and a step of canceling the pressing force. This makes it possible to measure blood pressures in a short time without causing a user to feel troublesome and to present the measured blood pressure to the user.

In the flowchart shown in FIG. 12, an optimum pressure sensor and an optimum pressing force are determined again at step S22. However, an alternative procedure is possible in which the control unit 12 determines an optimum pressure sensor and an optimum pressing force on the basis of pressure pulse waves that were detected by the respective pressure sensors 6a and 7a in a pressing force decreasing process started at step S9 in FIG. 6 and sets the thus-determined information as pressure pulse wave detection conditions to be used in a continuous blood pressure measurement.

More specifically, steps S21-S23 shown in FIG. 12 are omitted and the optimum pressing force that was determined in the pressing force decreasing process (step S9 and the following steps) is set at step S24. The control unit 12 acquires a pressure pulse wave that is detected by the optimum pressure sensor that was determined in the pressing force decreasing process (step S9 and the following steps), in a state that the sensor unit 6 is pressed toward the radius artery T with the thus-set optimum pressing force.

The above operation also makes it possible to shorten the time to completion of a first-beat blood pressure measurement as well as to reduce the power consumption.

In the operations shown in FIGS. 6 and 12, a transition is made to step S21 after the execution of step S12 with the rotation of the rotary member 5 maintained. A modification is possible in which the rotary member 5 is returned to the initial state after the execution of step S12, steps S1-S8 shown in FIG. 6 are thereafter executed instead of step S21, and then step S22 is executed.

In the above description, pulse wave envelope data is data that correlates a pressing force that the sensor unit 6 exerts toward the radius artery T with the amplitude of a pressure pulse wave that is detected by an optimum pressure sensor in a state that the sensor unit 6 is pressed toward the radius artery T by this pressing force. However, the invention is not limited to this case.

For example, the pulse wave envelope data may be data that correlates the amplitude of a pressure pulse wave that is detected by an optimum pressure sensor with a maximum pressure value (Morax shown in FIG. 10) of this pressure pulse wave. Alternatively, the pulse wave envelope data may be data that correlates the amplitude of a pressure pulse wave that is detected by an optimum pressure sensor with a minimum pressure value (Mmin shown in FIG. 10) of this pressure pulse wave. As a further alternative, the pulse wave envelope data may be data that correlates the amplitude of a pressure pulse wave that is detected by an optimum pressure sensor with the average of a maximum pressure value and a minimum pressure value of this pressure pulse wave. The average of a maximum pressure value and a minimum pressure value of a pressure pulse wave is information that defines the shape of this pressure pulse wave.

That is, the pulse wave envelope data may be data that correlates the amplitude value of a pressure pulse wave that is detected by an optimum pressure sensor in a process that the pressing force that the pressing surface 6b exerts toward the radius artery T is varied with information (e.g., Mmax, Mmin, or their average) other than the amplitude value among information that define the shape of this pressure pulse wave.

Irrespective of which of the above information the horizontal axis of the pulse wave envelope data represents, the information (i.e., Mmax and Mnin) that are used for generation of calibration data at step S12 in FIG. 6 are not limited to information of a pressure pulse wave having a maximum amplitude.

For example, it is possible to detect a portion of a pulse wave envelope in which the amplitude is larger than a certain level and approximately flat and use pressure pulse wave information corresponding this portion to generate calibration data.

Although in the embodiment the rotary member 5 is configured so as to be rotatable about each of the rotation axes X and Y, the rotary member 5 may be configured so as to be rotatable about one of the rotation axes X and Y.

Where the rotary member 5 is configured so as to be rotatable about only the rotation axis X, an appropriate operation that the control unit 12 is to perform is to omit steps S1A-S1C and execute step S2 after step S1. Even with this configuration and operation, a highly accurate blood pressure calculation can be performed because of the presence of step S6-S8.

Where the rotary member 5 is configured so as to be rotatable about only the rotation axis X, one of the element array of the pressure sensors 6a or the element array of the pressure sensors 7a may be omitted. Although the presence of two element arrays is preferable because it increases the probability that the artery is closed, even with only one element array the accuracy of a blood pressure calculation can be increased by controlling the rotation about the rotation axis X following a movement of the radius artery T.

Where the rotary member 5 is configured so as to be rotatable about only the rotation axis Y, an appropriate operation that the control unit 12 is to perform is to omit steps S6-S8 and execute step S9 after step S3. Even with this configuration and operation, an optimum pressure sensor can be determined with higher accuracy because of the presence of steps S1A-S1C which, for example, makes it possible to increase the amount of information that is necessary for determination of an optimum pressure sensor in a subsequent pressing force decreasing process.

Although the pressure pulse wave detection unit 100 is configured in such a manner that the one pressing surface is formed with the element array of the plural pressure sensors 6a and the element array of the plural pressure sensors 7a, the pressure pulse wave detection unit 100 may be configured in such a manner that its pressing surface is divided into plural surfaces which are formed with respective element arrays.

With the configuration in which the pressing surface is divided into plural surfaces, the degree of freedom of designing of the pressure pulse wave detection unit 100 is increased, which facilitates, for example, structure-related designing for improving the state of contact of the pressing surface to a skin. And, for example, improvement in the closeness of attachment is expected. On the other hand, in the configuration shown in FIG. 2, a pressing force can be transmitted to the artery with a higher degree of uniformity and hence improvement in the accuracy of a blood pressure measurement is expected.

Although in the example of FIG. 4 the rotation axis Y is set between the element array of the plural pressure sensors 6a and element array of the plural pressure sensors 7a, the invention is not limited to this case. For example, the rotation axis Y may be set outside the element array of the plural pressure sensors 6a and element array of the plural pressure sensors 7a.

More specifically, in FIG. 4, the rotation axis Y may be set on the left of the element array of the plural pressure sensors 6a. Alternatively, in FIG. 4, the rotation axis Y may be set on the right of the element array of the plural pressure sensors 7a.

Also with regard to the example of FIG. 4, although in this example the rotation axis X is set at such a position as to divide each of the two element arrays into equal halves, the invention is not limited this case. For example, the rotation axis X may be set at any position as to cross the element arrays at any position. As a further alternative, the rotation axis X may be set at such a position as not to cross either element array (i.e., at a top position or a bottom position of the sensor unit 6).

Figure 13:
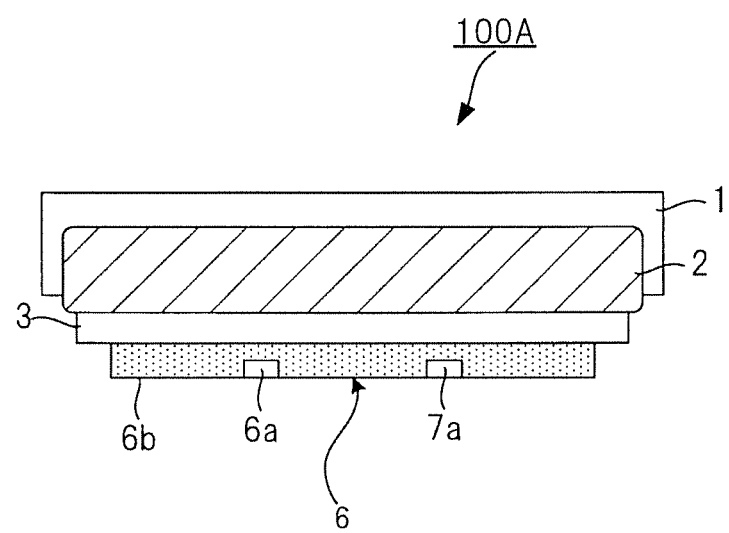
FIG. 13 is a diagram for showing the configuration of a pressure pulse wave detection unit 100A which is a modification of the pressure pulse wave detection unit 100.

Although in the pressure pulse wave detection unit 100 the pressing surface 6*b* is rotatable about the rotation axes X and Y, another configuration is possible in which as in a pressure pulse wave detection unit 100A shown in FIG. 13 the sensor unit 6 is directly fixed to the flat plate member 3.

Figure 14:
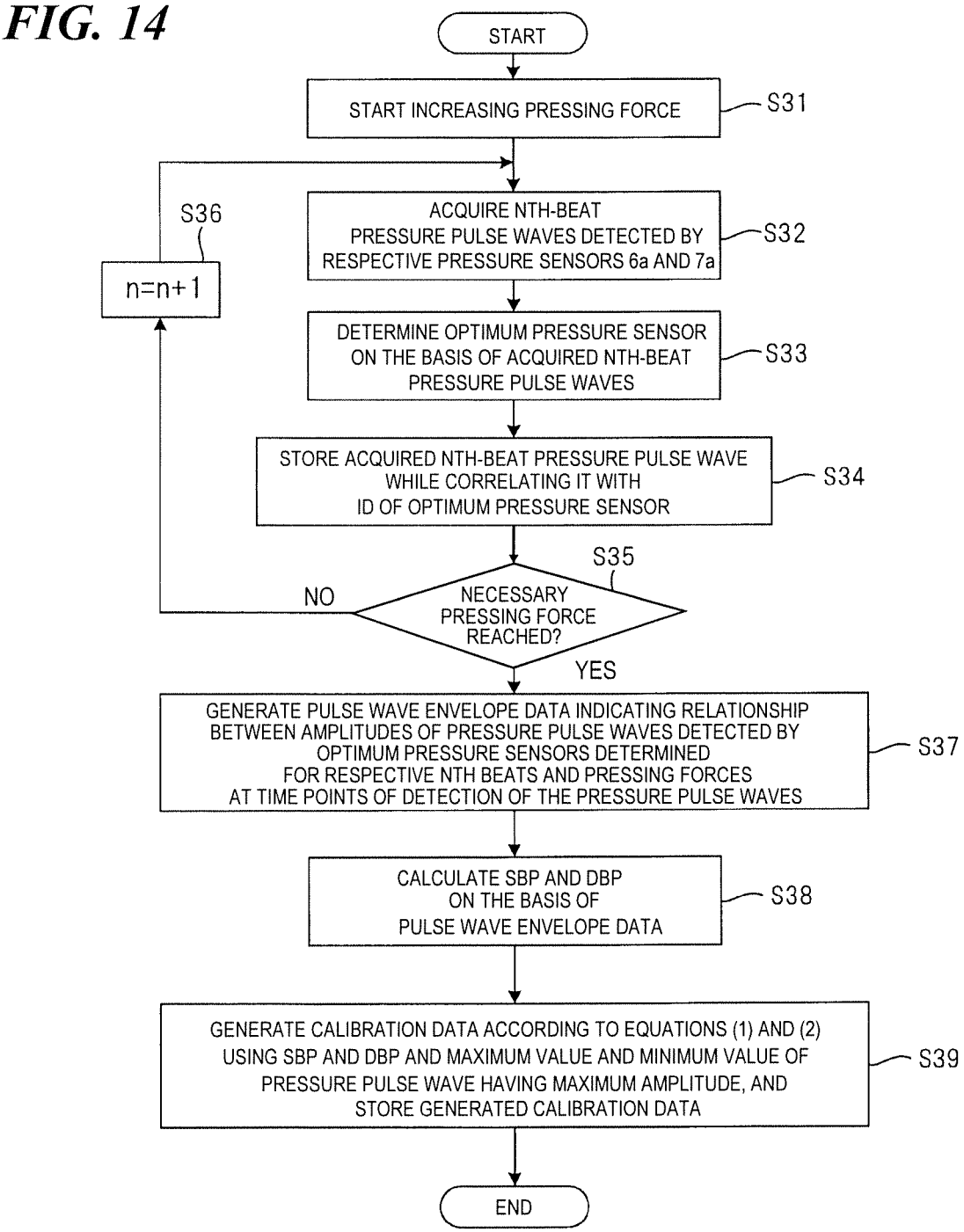
FIG. 14 is a flowchart for illustrating an example calibration blood pressure calculating operation of a pressure measurement device that employs the pressure pulse wave detection unit 100A instead of the pressure pulse wave detection unit 100.

FIG. 14 is a flowchart for illustrating an example operation, to generation of calibration data, of a pressure measurement device that employs the pressure pulse wave detection unit 100A instead of the pressure pulse wave detection unit 100.

Upon reception of a blood pressure measurement instruction, the control unit 12 controls the air bag drive unit 11 to start injecting air into the air bag 2 and thereby increases the pressing force that the pressing surface 6*b* exerts toward the radius artery T (step S31).

Then the control unit 12 acquires nth-beat pressure pulse waves (n is a natural number that is larger than or equal to 1 and has an initial value "1") detected by the respective pressure sensors 6*a* and 7*a* (step S32).

Then the control unit 12 determines an optimum pressure sensor on the basis of the acquired nth-beat pressure pulse waves among the pressure sensors 6*a*, 7*a* (step S33). For example, the control unit 12 determines, as an optimum pressure sensor, a pressure sensor that detected a pressure pulse wave having a maximum amplitude among the pressure pulse waves acquired at step S32.

Also in this configuration, plural pressure sensors may be found that detected pressure pulse waves having a maximum amplitude. In this case, an appropriate course of action is to deal with these plural pressure sensors as optimum pressure sensors and employ an average, for example, of the pressure pulse waves detected by these respective plural pressure sensors as a "pressure pulse wave detected by an optimum pressure sensor."

Even if only one pressure sensor detected a pressure pulse wave having a maximum amplitude among the pressure pulse waves acquired at step S32, this pressure sensor and pressure sensors located in the vicinity of (e.g., immediately adjacent, from both sides, to) this pressure sensor may be dealt with as optimum pressure sensors. Also in this case, an average, for example, of the pressure pulse waves detected by these respective plural pressure sensors may be employed as a "pressure pulse wave detected by an optimum pressure sensor."

Then the control unit 12 stores the value of n, an identification ID of the determined pressure sensor, the nth-beat pressure pulse wave detected by the optimum pressure sensor, and the pressing force (the internal pressure of the air bag 2) at a time point of detection of this pressure pulse wave in the memory 15 in such a manner that they are correlated with each other (step S34). The identification ID of a pressure sensor is information indicating the element array to which the pressure sensor belongs and a position of the pressure sensor in the element array.

Subsequently, the control unit 12 judges whether the pressing force has reached a value that is necessary to close the radius artery T. If the pressing force has not reached the necessary pressing force yet (step S35: no), the control unit 12 updates n to n+1 (step S36) and returns to step S32.

If the pressing force has reached the necessary pressing force yet (step S35: yes), at step S37 the control unit 12 generates pulse wave envelope data indicating a relationship between the amplitudes of pressure pulse waves detected by optimum pressure sensors corresponding to respective nth beats and internal pressures of the air bag 2 at time points of detection of these pressure pulse waves (i.e., information stored in the memory 15).

Then, at step S38, the control unit 12 calculates SBP and DBP on the basis of the generated pulse wave envelope data by the same method as employed at step S11.

Subsequently, the control unit 12 calculates coefficients a and b according to Equations (1) and (2) using the calculated SBP and DBP and a maximum value Mmax and a minimum value Mmin of a pressure pulse wave having a maximum amplitude in the pulse wave envelope data generated at step S37, and stores the coefficients a and b and Equations (1) and (2) in the memory 15 as calibration data (step S39).

After the execution of step S39, the control unit 12 releases the air from inside the air bag 2 and then calculates second blood pressure values for each beat by executing step S21 and the following steps shown in FIG. 12.

Alternatively, after the execution of step S39, the control unit 12 determines, as an optimum pressure sensor for a continuous blood pressure measurement, the pressure sensor, that detected the pressure pulse wave having the maximum amplitude, among the n optimum pressure sensors having the identification IDs stored in the memory 15. And the control unit 12 determines, as an optimum pressing force for a continuous blood pressure measurement, the pressing force at the time point of detection of the pressure pulse wave by the optimum pressure sensor for a continuous blood pressure measurement.

Then the control unit 12 measures blood pressure values for each beat by calibrating, using the calibration data generated at step S39, a pressure pulse wave detected by the optimum pressure sensor for a continuous blood pressure measurement in a state that the internal pressure of the air bag 2 is set at a pressure corresponding to the optimum pressing force for a continuous blood pressure measurement.

In the example operation shown in FIG. 14, blood pressure values for generation of calibration data are calculated on the basis of pressure pulse waves that were detected by the pressure sensors in a pressing force increasing process. On the other hand, as described above, it is also possible to generate pulse wave envelope data on the basis of pressure pulse waves that are detected by the pressure sensors in a process that the pressing force is decreased after it was increased until the radius artery T was closed sufficiently and then calculate blood pressure values for generation of calibration data on the basis of the pulse wave envelope data.

As described above, in the pressure measurement device that employs the pressure pulse wave detection unit 100A instead of the pressure pulse wave detection unit 100, blood pressures can be calculated on the basis of pressure pulse waves that were detected by the pressure sensors in a process that the pressing force was increased or decreased. As a result, a blood pressure measurement can be performed in a short time while the load of a user is lowered.

In the operation shown in FIG. 14, a pressure sensor that detected a maximum pulse wave amplitude among all of the pressure sensors 6*a* and 7*a* at each of different time points in a process that the pressing force is increased or decreased is determined as an optimum pressure sensor. As a result, even if the radius artery T is moved in the direction B in the pressing force increasing or decreasing process, the optimum pressure sensor varies following the movement of the radius artery T. This enables a highly accurate blood pressure calculation that follows a movement of the radius artery T. The pressure pulse wave detection unit 100A can realize this advantage without using the rotary member 5 or biaxial rotating mechanism 5a. Thus, the blood pressure measurement device can be made even smaller.

As in the case of the pressure pulse wave detection unit 100, the pressure pulse wave detection unit 100A may be configured in such a manner that one of the two element arrays is eliminated or the two element arrays are formed in different pressing surfaces.

Figure 15:
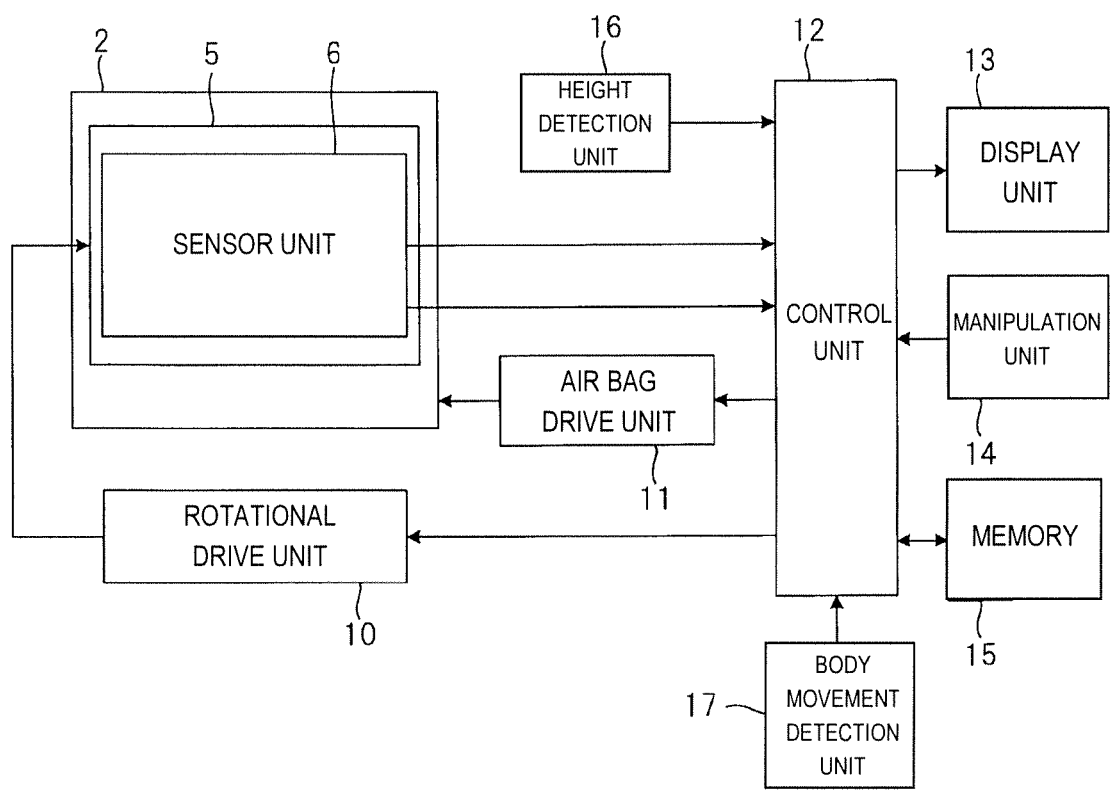
FIG. 15 is a diagram for showing a modification of the block configuration of the blood pressure measurement device shown in FIG. 5.

FIG. 15 is a diagram for showing a modification of the block configuration of the blood pressure measurement device shown in FIG. 5. The blood pressure measurement device shown in FIG. 15 is the same in configuration as that shown in FIG. 5 except that the former is added with a height detection unit 16 and a body movement detection unit 17.

The height detection unit 16 detects a height, with respect to a reference position, of a living body part to which the blood pressure measurement device is attached. The height detection unit 16 is, for example, an acceleration sensor or a barometric pressure sensor and the reference position is a height 0 m, for example.

The body movement detection unit 17 detects a movement of a living body part to which the blood pressure measurement device is attached. The body movement detection unit 17 is, for example, a combination of a triaxial acceleration sensor, a triaxial angular velocity sensor, and a triaxial geomagnetism sensor and detects a movement of a living body part in detail. The body movement detection unit 17 may employ sensors that are suitable for necessary movement detection accuracy.

An operation to generation of calibration data of the blood pressure measurement device shown in FIG. 15 is almost the same as the operation shown in FIG. 6. A difference from the operation shown in FIG. 6 is that the control unit 12 stores the following three kinds of information in the memory 15 after calculating SBP and DBP at step S11.

The three kinds of information are information of a height that was detected by the height detection unit 16 in a period of detection of a pressure pulse wave that was used for generation of pulse wave envelope data at step S10 (i.e., a height of the device attachment part when a pressure pulse wave for generation of calibration data was detected), information of a movement that was detected by the body movement detection unit 17 in the period of detection of the pressure pulse wave that was used for generation of the pulse wave envelope data at step S10 (i.e., a movement of the device attachment part when the pressure pulse wave for generation of the calibration data was detected), and an identification ID of an optimum pressure sensor that detected the pressure pulse wave that was used for generation of the pulse wave envelope data at step S10 (i.e., a pressure sensor that output the pressure pulse wave that was used for generation of the calibration data).

Figure 16:
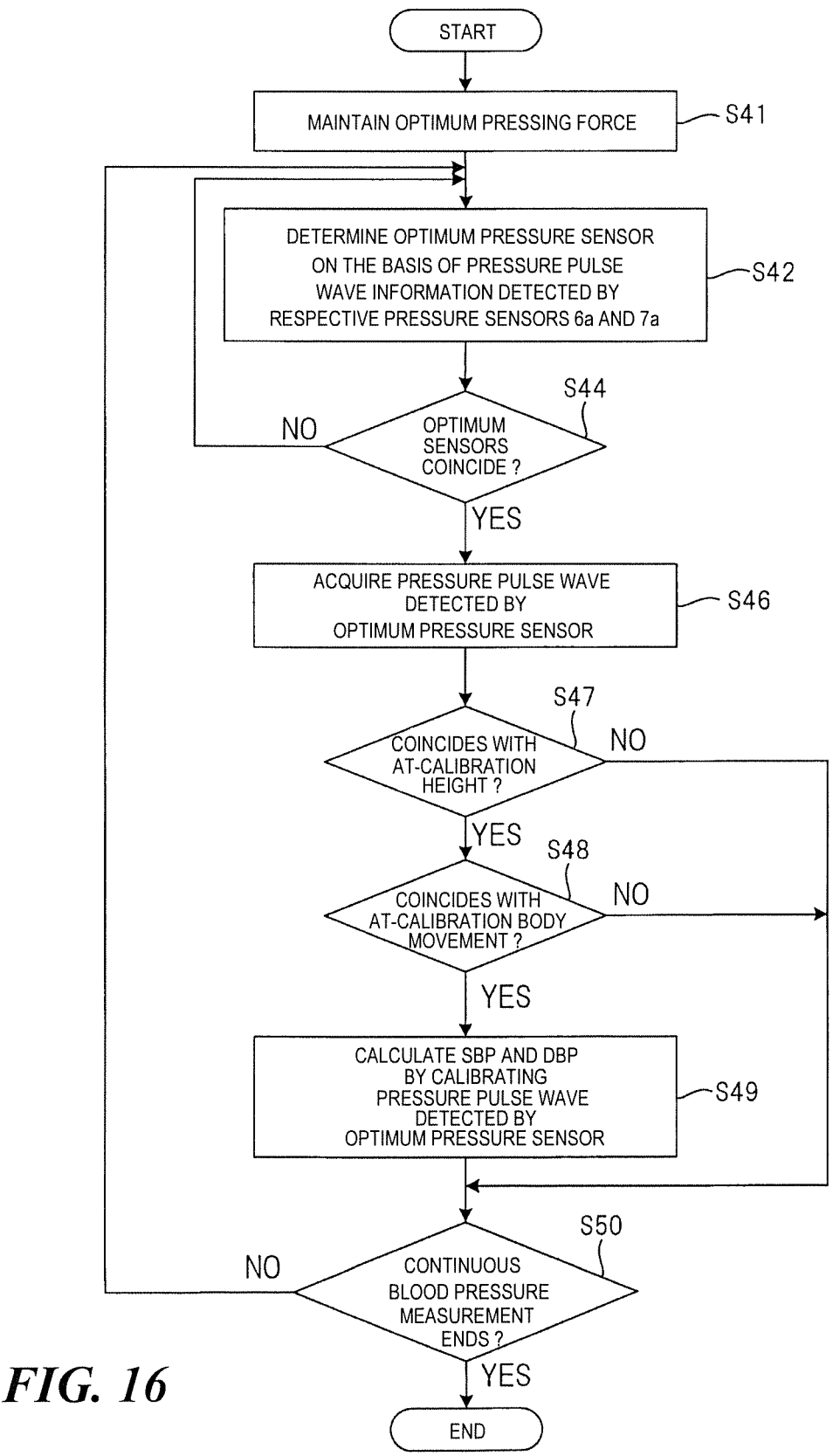
FIG. 16 is a flowchart for illustrating a continuous blood pressure measuring operation (i.e., an operation that is performed after generation of calibration data) of the blood pressure measurement device shown in FIG. 15.

FIG. 16 is a flowchart for illustrating a continuous blood pressure measuring operation (i.e., an operation that is performed after generation of calibration data) of the blood pressure measurement device shown in FIG. 15.

The control unit 12 controls the air bag drive unit 11 so that the internal pressure of the air bag 2 is increased to the optimum pressing force that was determined at step S9 and the following steps shown in FIG. 6, and maintains the optimum pressing force (step S41).

Then the control unit 12 determines, as an optimum pressure sensor, one, detecting a pressure pulse wave having a maximum amplitude, of the pressure sensors 6a and 7a (step S42).

Subsequently, the control unit 12 compares the identification ID of the optimum pressure sensor that was stored at step S11 in FIG. 6 with that of the optimum pressure sensor determined at step S42. If they coincide with each other (step S44: yes), the control unit 12 moves to step S46. If they do not coincide with each other (step S44: no), the control unit 12 returns to step S42.

At step S46, the control unit 12 acquires the pressure pulse wave being detected by the optimum pressure sensor. Then the control unit 12 compares a height that is detected by the height detection unit 16 at the same time as the pressure pulse wave acquired at step S46. If they coincide with each other (step S47: yes), the control unit 12 moves to step S48. If they do not coincide with each other (step S47: no), the control unit 12 moves to step S50.

At step S48, the control unit 12 compares movement information that is detected by the body movement detection unit 17 at the same time as the pressure pulse wave acquired at step S46. If they coincide with each other (step S48: yes), the control unit 12 moves to step S49. If they do not coincide with each other (step S48: no), the control unit 12 moves to step S50.

Coincidence between two heights means that they coincide with each other substantially, that is, the difference between the two heights is smaller or equal to a threshold THc. Coincidence between two movements means that they coincide with each other substantially, that is, the difference between the two movements is smaller or equal to a threshold THd. The threshold THc and the threshold THd may be set as appropriate according to measurement accuracy that is required for blood pressure values to be calculated at step S49.

At step S49, the control unit 12 calculates SBP and DBP by calibrating the one pressure pulse wave acquired at step S46 using the calibration data that was generated at step S12 in FIG. 6.

At the following step S50, the control unit 12 finishes the process if receiving an instruction to finish the continuous blood pressure measurement, and returns to step S42 if not receiving an end instruction.

As described above, in the blood pressure measurement device shown in FIG. 15, SBP and DBP are calculated by calibrating a calibration target pressure pulse wave only in a case that detection conditions of the calibration target pressure pulse wave coincide with detection conditions under which a pressure pulse wave for generation of calibration data was detected.

The detection conditions under which a pressure pulse wave for generation of calibration data was detected include the above three kinds of information. And the detection conditions of a calibration target pressure pulse wave include the identification ID of an optimum pressure sensor that detects the calibration target pressure pulse wave, a height of a device attachment part at a time point of detection of the calibration target pressure pulse wave, and a movement of the device attachment part at the time point of detection of the calibration target pressure pulse wave.

Since as described above a blood pressure calculation is performed by calibrating a calibration target pressure pulse wave only when detection conditions of a pulse wave in a continuous blood pressure measurement coincide with detection conditions under which a pressure pulse wave for generation of calibration data was detected, the calibration accuracy and hence the accuracy of a blood pressure measurement can be increased.

Although the three conditions (pressure sensor identification ID, height, movement) were used above as detection conditions for comparison, it suffices that the detection conditions include at least one of the three conditions.

Information of a height of a device attachment part when a pressure pulse wave for generation of calibration data was detected (one of the above conditions) is a typical value (e.g., average) of heights that were measured by the height detection unit 16 when pressure pulse waves for generation of calibration data were detected.

Likewise, information of a movement of a device attachment part when a pressure pulse wave for generation of calibration data was detected is a typical value (e.g., average) of movements that were measured by the body movement detection unit 17 when pressure pulse waves for generation of calibration data were detected.

The pressure pulse wave detection unit 100 of the blood pressure measurement device shown in FIG. 15 may be replaced by the pressure pulse wave detection unit 100A shown in FIG. 13. In this case, an operation to generation of calibration data is almost the same as the operation shown in FIG. 14. In this case, an appropriate action that the control unit 12 is to perform after calculating SBP and DBP at step S38 is to store, in the memory 15, as detection conditions of a pressure pulse wave used for generation of calibration data, information of a height that was detected by the height detection unit 16 at a time point of detection of pressure pulse waves of pulse wave envelope data generated at step S37 (i.e., average height), information of a movement that was detected by the body movement detection unit 17 at the time point of detection of the pressure pulse waves of the pulse wave envelope data generated at step S37 (i.e., average movement), an identification ID of an optimum pressure sensor that detected one, having a maximum amplitude, of the pressure pulse waves of the pulse wave envelope data generated at step S37, and a pressing force at the time point of detection of the pressure pulse wave having a maximum amplitude.

At step S41 in FIG. 16, the control unit 12 may keep the internal pressure of the air bag 2 at the pressing force that was stored at step S38, for example.

Figure 17:
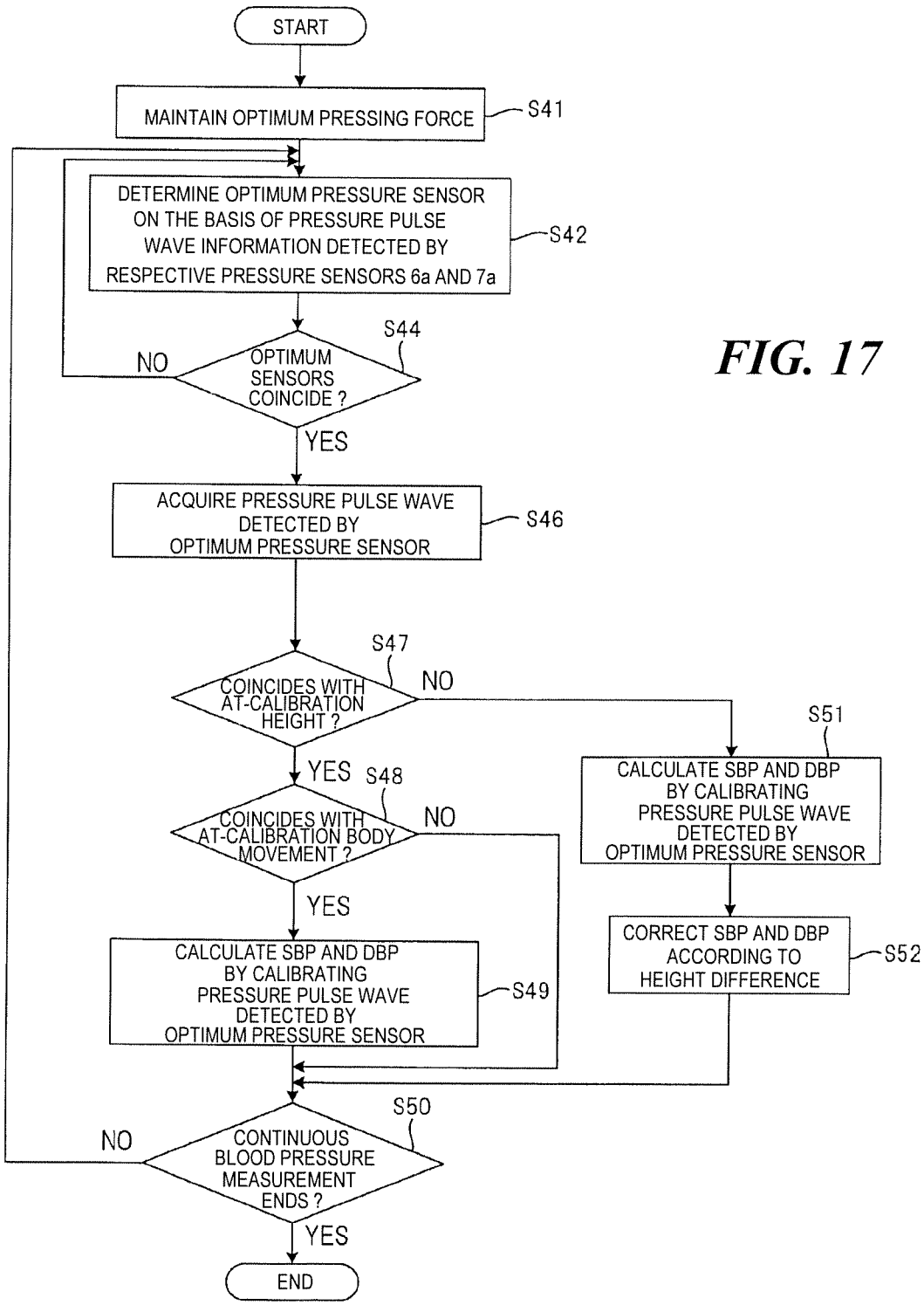
FIG. 17 is a flowchart for illustrating a modification of the continuous blood pressure measurement operation of the blood pressure measurement device shown in FIG. 15.

FIG. 17 is a flowchart for illustrating a modification of the continuous blood pressure measurement operation of the blood pressure measurement device shown in FIG. 15. Steps in FIG. 17 having the same ones in FIG. 16 are given the same symbols as the latter, and descriptions therefor will be omitted.

If making a negative judgment at step S47, the control unit 12 calculates SBP and DBP by calibrating a pressure pulse wave detected by an optimum pressure sensor determined at step S42 using calibration data (step S51).

Then, at step S52, the control unit 12 corrects the SBP and the DBP calculated at step S51 according to the difference between a height detected by the height detection unit 16 when the pressure pulse wave acquired at step S46 was detected and a height that was stored at step S11 in FIG. 6 or step S38 in FIG. 14. Then the control unit 12 executes step S50.

In a continuous blood pressure measurement, blood pressures are calculated by calibrating a pressure pulse wave detected by an optimum pressure sensor. Thus, if a height of a device attachment part when the pressure pulse wave acquired at step S46 was detected is different from a height of the device attachment part at a time of generation of calibration data, a calibrated blood pressure may include an error due to the height difference.

In the blood pressure measurement device shown in FIG. 15, calibration data is generated in a state that the wrist is set at the same height as the heart. If two arteries have a height difference $\Delta H$ (cm), a pressure difference obtained by multiplying the water head pressure per unit length (=0.8 mmHg/cm) by $\Delta H$ occurs between the two arteries.

Thus, at step S52, the control unit 12 performs a blood pressure correction by adding or subtracting, to or from SBP and DBP calculated at step S51, a value obtained by multiplying the water head pressure per unit length by a difference $\Delta H$ between a height of a device attachment part when a pressure pulse wave was detected by an optimum pressure sensor in the continuous blood pressure measurement and a height of the device attachment part at a time point of generation of calibration data.

As described above, if a pressure pulse wave is detected with a height that is different from a height detected at a time point of generation of calibration data, blood pressure values obtained by calibrating this pressure pulse wave are corrected according to the difference between the wrist height at the time point of detection of the pressure pulse wave and that at the time point of generation of the calibration data, whereby a highly accurate blood pressure measurement is enabled.

Also in the modifications described above with reference to FIGS. 15 to 17, the pressure pulse wave detection unit 100 may be provided with only one element array. As a further alternative, the pressure pulse wave detection unit 100 may be configured so as to have two pressing surfaces that are formed with respective element arrays.

In the flowcharts of FIGS. 16 and 17, no blood pressure measurement is performed if a negative judgment is made at step S44. In this connection, a modification is possible in which if a negative judgment is made at step S44 or a negative judgment is made repeatedly a prescribed number of times at step S44, the process is returned to step S1 in FIG. 6, that is, generation of calibration data is generated again (steps S1-S12). In the blood pressure measurement device according to the embodiment, calibration data can be generated easily. Thus, a highly accurate continuous blood pressure measurement is enabled by generating calibration data again.

Likewise, in the flowchart of FIG. 16, if a negative judgment is made at step S47 or a negative judgment is made repeatedly a prescribed number of times at step S47, the process may be returned to step S1 in FIG. 6. Furthermore, in the flowcharts of FIGS. 16 and 17, if a negative judgment is made at step S48 or a negative judgment is made repeatedly a prescribed number of times at step S48, the process may be returned to step S1 in FIG. 6.

The processes shown in FIGS. 6, 12, 14, 16 and 17 which are executed by the control unit 12 can be implemented as programs for causing a computer to execute their individual steps. Such programs are recorded in a computer-readable, non-transitory recording medium.

Such a computer-readable recording medium includes an optical medium such as a CD-ROM (compact disc-ROM) and a magnetic recording medium such as a memory card. It is also possible to provide such programs by downloading them over a network.

The embodiment disclosed above should be construed in all respects as being illustrative and not being restrictive. The scope of the invention is defined by the claims rather than the above description, and it is intended that the scope of the invention includes all changes that are within the range of the claims and their equivalents.

As described above, the following items are disclosed in this specification.

The disclosed blood pressure measurement device comprises at least one element array of plural pressure detecting elements arranged in one direction; a pressing unit which presses the at least one element array against a skin of a living body toward an artery in a state that the one direction crosses a direction in which the artery runs; a pressing control unit which controls a pressing force of the pressing unit; and a first blood pressure calculation unit which calculates first blood pressure values in the artery on the basis of pressure pulse waves that were detected by the respective pressure detecting elements included in the at least one element array in a process that the pressing force was increased or decreased by a control of the pressing control unit.

In the disclosed blood pressure measurement device, the first blood pressure calculation unit selects at least one of the pressure detecting elements included in the at least one element array at each of plural time points in a process that the pressing force is increased or decreased on the basis of pressure pulse waves that were detected by the respective pressure detecting elements included in the at least one element array, and calculates first blood pressure values in the artery on the basis of amplitude variations of pressure pulse waves that were detected at the plural time points by the pressure detecting elements selected at the plural time points, respectively.

The disclosed blood pressure measurement device further comprises a calibration data generation unit which generates calibration data using the first blood pressure values calculated by the first blood pressure calculation unit; and a second blood pressure calculation unit which calculates second blood pressure values in the artery by calibrating, using the calibration data, a pressure pulse wave that is detected by one pressure detecting element selected from the pressure detecting elements included in the at least one element array in a state that the at least one element array is pressed toward the artery with such a pressing force as to deform part of the artery into a flat shape.

In the disclosed blood pressure measurement device, the calibration data generation unit generates calibration data using a pressure pulse wave selected from the pressure pulse waves that were detected at the plural time points by the pressure detecting elements selected at the plural time points, respectively, and the first blood pressure values.

In the disclosed blood pressure measurement device, the first blood pressure calculation unit generates pulse wave envelope data that correlates amplitude values of the pressure pulse waves that were detected at the plural time points by the pressure detecting elements selected at the plural time points, respectively, with pressure values when the respective pressure pulse waves were detected or information that define shapes of the pressure pulse waves other than the amplitude values, respectively, and calculates first blood pressure values on the basis of the pulse wave envelope data.

The disclosed blood pressure measurement device includes one in which the information that define shapes of the pressure pulse waves other than the amplitude values are maximum values of the pressure pulse waves, minimum values of the pressure pulse waves, or respective average values of the maximum values and the minimum values.

The invention can provide a blood pressure measurement device capable of measuring a blood pressure with high accuracy in a short time without causing a user to feel troublesome.

Although the invention has been described above using the particular embodiment, the invention is not limited to this embodiment. Various modifications are possible without departing from the technical concept of the disclosed invention.

The invention claimed is:

1. A blood pressure measurement device including:
at least one element array of plural pressure detecting sensors arranged in one direction;
a pressing unit which presses the at least one element array of pressure detecting sensors against a skin of a living body toward an artery in a state that the one direction crosses a direction in which the artery runs; and
a processor configured to perform:
controlling a pressing force of the pressing unit;
calculating first blood pressure values in the artery on the basis of pressure pulse waves that were detected by the respective pressure detecting sensors included in the at least one element array of pressure detecting sensors in a process that the pressing force was increased or decreased by a control of the processor;
obtaining pressure pulse waves detected by the respective pressure detecting sensors included in the at least one element array of pressure detecting sensors,
selecting, based on first obtained pressure pulse waves, at least one of the pressure detecting sensors included in the at least one element array of pressure detecting sensors at a first time point during the process of increasing the pressing force; and
re-selecting, based on second obtained pressure pulse waves, at least one of the pressure detecting sensors included in the at least one element array of the pressure detecting sensors at a second time point during the process of increasing the pressing force,
wherein the first time point and second time point are different time points, and
wherein the processor
calculates first blood pressure values in the artery on the basis of first pressure pulse waves that were detected by the pressure detecting sensors corresponding to the different time points, respectively,
generates calibration data using the first blood pressure values calculated by the processor, and
calculates second blood pressure values in the artery by calibrating, using the calibration data, a pressure pulse wave that is detected by one pressure detecting sensor selected from the pressure detecting sensors included in the at least one element array of pressure detecting sensors in a state that the at least one element array of pressure detecting sensors is pressed toward the artery with such a pressing force as to deform part of the artery into a flat shape.

2. The blood pressure measurement device of claim 1, wherein the processor calculates the first blood pressure values in the artery on the basis of amplitude variations of the first pressure pulse waves, respectively.

3. The blood pressure measurement device of claim 1, wherein the processor generates the calibration data using the pressure pulse wave selected from the first pressure pulse waves, and the first blood pressure values.

4. The blood pressure measurement device of claim 1, wherein the processor
generates pulse wave envelope data that correlates amplitude values of the first pressure pulse waves with pressure values when the respective first pressure pulse waves were detected, respectively, or pulse wave envelope data that correlates the amplitude values of the first pressure pulse waves with information that defines shapes of the pressure pulse waves other than the amplitude values, respectively, and calculates the first blood pressure values on the basis of the pulse wave envelope data.

5. The blood pressure measurement device of claim 4, wherein the information that define shapes of the pressure pulse waves other than the amplitude values are
maximum values of the first pressure pulse waves,
minimum values of the first pressure pulse waves, or
respective average values of the maximum values and the minimum values.

6. The blood pressure measurement device of claim 1, wherein the processor
selects at least one pressure detecting sensor included in the at least one element array of pressure detecting sensors at the first time point during the process of increasing the pressing force,
re-selects at least one pressure detecting sensor included in the at least one element array of pressure detecting sensors at the second time point during the process of increasing the pressing force, and
wherein at least one pressure detecting sensor selected at the first time point is different from at least one pressure detecting sensor re-selected at the second time point.

7. The blood pressure measurement device of claim 6, wherein the processor iteratively performs selecting and re-selecting of at least one of the pressure detecting sensors included in the at least one element array of pressure detecting sensors at a plurality of different time points throughout the process of increasing the pressing force.

8. The blood pressure measurement device of claim 7, wherein, at respective different time points that the processor performs selecting and re-selecting of at least one of the pressure detecting sensors included in the at least one element array of pressure detecting sensors at the plurality of different time points throughout the process of increasing the pressing force,
at least one pressure detecting sensor selected is different from at least one pressure detecting sensor re-selected at the second time point, and/or
at least one pressure detecting sensor selected is the same as at least one pressure detecting sensor re-selected at the second time point.

9. The blood pressure measurement device of claim 1, wherein the processor iteratively performs selecting and re-selecting of at least one of the pressure detecting sensors included in the at least one element array of pressure detecting sensors at a plurality of different time points throughout the process of increasing the pressing force.

10. The blood pressure measurement device of claim 9, wherein, at respective points of the different time points that the processor performs selecting and re-selecting of at least one of the pressure detecting sensors included in the at least one element array of pressure detecting sensors at the plurality of different time points throughout the process of increasing the pressing force,
at least one pressure detecting sensor selected is different from at least one pressure detecting sensor re-selected, and
at least one pressure detecting sensor selected is the same as at least one pressure detecting sensor re-selected.

* * * * *